US006432690B1

(12) United States Patent
Xu et al.

(10) Patent No.: US 6,432,690 B1
(45) Date of Patent: Aug. 13, 2002

(54) HUMAN ASPARTIC PROTEASES

(75) Inventors: Hong Xu; Sandra A. Bruno; Laura A. Elsenboss, all of Mystic; Michael Fogliano, Old Lyme; Victoria L. Cohan, East Lyme, all of CT (US); Olga Bandman, Mountain View, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/705,448

(22) Filed: Nov. 2, 2000

Related U.S. Application Data

(60) Division of application No. 09/116,641, filed on Jul. 16, 1998, which is a continuation-in-part of application No. 09/008,271, filed on Jan. 16, 1998, now Pat. No. 6,203,979.

(51) Int. Cl.[7] .......................... C12N 9/64; C12N 15/57

(52) U.S. Cl. ................ 435/226; 435/252.3; 435/320.1; 435/6; 536/23.2

(58) Field of Search ............................ 435/226, 320.1, 435/6, 252.3; 536/23.2

(56) References Cited

U.S. PATENT DOCUMENTS 5,776,759 A * 7/1998 Bandman et al. ........... 435/226
6,225,103 B1 * 5/2001 Keolsch et al. ............. 435/226

FOREIGN PATENT DOCUMENTS

WO WO 98/11236 3/1998
WO WO 98/22597 5/1998

OTHER PUBLICATIONS

Tatnell, P.J. et al., "Napsins: new human aspartic proteinases", *FEBS Letters*, 441:43–48, (1998).

Koelsch, G. et al., "New human aspartic proteases napsin 1 and 2: Molecular cloning and intracellular localization of napsin 1", Database EMHUM1 (Online) EMBL, Accession No. AF098485, Feb. 8, 1999.

Beynon, R.J. and J.S. Bond, *Proteolytic Enzymes: A Practical Approach*, Oxford University Press, New York, NY, pp. 1–5 (1994).

von Heijne, G., "A new method for predicting signal sequence cleavage sites", *Nuc. Acid. Res.*, 14: 4683–4690 (1986).

Zunino, S. J. et al., "RNKP–1, A Novel Natural Killer–Associated Serine Protease Gene Cloned From RNK–16 Cytotoxic Lymphocytes", *J. Immunol.*, 144: 2001–2009 (1990).

Sayers, T.J. et al., "Purification and Cloning of a Novel Serine Protease, RNK–Tryp–1, from the Granules of a Rat NK Cell Leukemia", *J. Immunol.*, 152: 2289–2297 (1994).

Keyszer, G.H. et al., "Comparative Analysis of Cathepsin L, Cathepsin D, and Collagenase Messenger RNA Expression in Synovial Tissues of Patients With Rheumatoid Arthritis and Osteoarthritis, By In Situ Hybridization", *Arthritis Rheum.*, 38: 976–984 (1995).

Chambers, A.F. and A.B. Tuck, "Ras–Responsive Genes and Tumor Matastasis", *Crit. Rev. Oncog.*, 4: 95–114 (1993).

Cuypers, H.T. et al., "Sulfhydryl Content of Bovine Eye Lens Leucine Aminopeptidase", *J. Biol. Chem.*, 257: 7086–7091 (1982).

Shelness, G.S. and G. Blobel, "Two Subunits of the Canine Signal Peptidase Complex Are Homologous to Yease SEC11 Protein", *J. Biol. Chem.*, 265: 9512–9519 (1990).

Ciechanover, A., "The Ubiquitin–Proteaseome Proteolytic Pathway", *Cell*, 79: 13–21 (1994).

Murphy, G., "The Regulation of Connective Tissue Metalloproteinases by Natural Inhibitors", *Agents Actions Suppl.*, 35: 69–76 (1991).

Calkins, C.C. and B.F. Sloane, "Mammaliam Cysteine protease Inhibitors: Biochemical Properties and Possible Roles in Tumor Progression", *Biol. Biochem. Hoppe Seyler*, 376: 71–80 (1995).

Tanaka, K. et al., (Direct Submission), GenBank Sequence Database (Accession M58593), National Center for Biotechnology Information National Library of Medcine, Bethesda, Maryland, 20894 (GI 203206; GI 203207).

Tsurumi, C. et al., (Direct Submission), GenBank Sequence Database (Accession D50063), National Center for Biotechnology Information, National Library of Medicine, Bethesda, Maryland 20894 (GI 971269; GI 971270) (1996).

Tsurumi, C. et al., (Direct Submission), GenBank Sequence Database (Accession 971270), National Center for Biotechnology Information, National Library of Medicine, Bethesda, Maryland, 20894 (GI 971270) (1998).

Tatnell, P.J. et al., "Napsins: new human aspartic proteinases Distinction between two closely related genes", *FEBS Letters*, 441: 43–48 (1998).

Databse EMHUM1 Online! EMBL Accession No AF098485, Feb. 8, 1999 Koelsch et al.: "New human aspartic proteases napsin 1 and napsin 2: Molecular cloning and intracellular localization of napsin1" XP002119587.

* cited by examiner

*Primary Examiner*—Charles L. Patterson, Jr.
(74) *Attorney, Agent, or Firm*—Incyte Genomics, Inc.

(57) ABSTRACT

The invention provides human aspartic proteases (NHAP) and polynucleotides which identify and encode NHAP. The invention also provides expression vectors, host cells, antibodies, agonists, and antagonists. The invention also provides methods for diagnosing, treating or preventing disorders associated with expression of NHAP.

13 Claims, 14 Drawing Sheets

```
                 9                    18                    27                    36                    45                    54
5' ATG TCT CCA CCA CCG CTG CTG CAA CCC CTG CTG CTG CTG CTG CCT CTG CTG AAT
   M   S   P   P   P   L   L   Q   P   L   L   L   L   L   P   L   L   N

                63                    72                    81                    90                    99                   108
   GTG GAG CCT TCC GGG GCC ACA CTG ATC CGC ATC CCT CTT CAT CGA GTC CAA CCT
   V   E   P   S   G   A   T   L   I   R   I   P   L   H   R   V   Q   P

               117                   126                   135                   144                   153                   162
   GGA CGC AGG ACC CTG AAC CTA CTG AGG GGA TGG AGA GAA CCA GCA GAG CTC CCC
   G   R   R   T   L   N   L   L   R   G   W   R   E   P   A   E   L   P

               171                   180                   189                   198                   207                   216
   AAG TTG GGG GCC CCA TCC CCT GGG GAC AAG CCC ATC TTC GTA CCT CTC TCG AAC
   K   L   G   A   P   S   P   G   D   K   P   I   F   V   P   L   S   N

               225                   234                   243                   252                   261                   270
   TAC AGG GAT GTG CAG TAT TTT GGG GAA ATT GGG CTG GGA ACG CCT CCA CAA AAC
   Y   R   D   V   Q   Y   F   G   E   I   G   L   G   T   P   P   Q   N

               279                   288                   297                   306                   315                   324
   TTC ACT GTT GCC TTT GAC ACT GGC TCC TCC AAT CTC TGG GTC CCG TCC AGG AGA
   F   T   V   A   F   D   T   G   S   S   N   L   W   V   P   S   R   R

               333                   342                   351                   360                   369                   378
   TGC CAC TTC TTC AGT GTG CCC TGC TGG TTA CAC CAC CGA TTT GAT CCC AAA GCC
   C   H   F   F   S   V   P   C   W   L   H   H   R   F   D   P   K   A
```

FIGURE 1A

```
        387         396         405         414         423         432
TCT AGC TCC TTC CAG GCC AAT GGG ACC AAG TTT GCC ATT CAA TAT GGA ACT GGG
S   S   S   F   Q   A   N   G   T   K   F   A   I   Q   Y   G   T   G

        441         450         459         468         477         486
CGG GTA GAT GGA ATC CTG AGC GAG GAC AAG CTG ACT ATT GGT GGA ATC AAG GGT
R   V   D   G   I   L   S   E   D   K   L   T   I   G   G   I   K   G

        495         504         513         522         531         540
GCA TCA GTG ATT TTC GGG GAG GCT CTC TGG GAG CCC AGC CTG GTC TTC GCT TTT
A   S   V   I   F   G   E   A   L   W   E   P   S   L   V   F   A   F

        549         558         567         576         585         594
GCC CAT TTT GAT GGG ATA TTG GGC CTC GGT TTT CCC ATT CTG TCT GTG GAA GGA
A   H   F   D   G   I   L   G   L   G   F   P   I   L   S   V   E   G

        603         612         621         630         639         648
GTT CGG CCC CCG ATG GAT GTA CTG GTG GAG CAG GGG CTA TTG GAT AAG CCT GTC
V   R   P   P   M   D   V   L   V   E   Q   G   L   L   D   K   P   V

        657         666         675         684         693         702
TTC TCC TTT TAC CTC AAC AGG GAC CCT GAA GAG CCT GAT GGA GGA GAG CTG GTC
F   S   F   Y   L   N   R   D   P   E   E   P   D   G   G   E   L   V

        711         720         729         738         747         756
CTG GGG GGC TCG GAC CCG GCA CAC TAC ATC CCA CCC CTC ACC TTC GTG CCA GTC
L   G   G   S   D   P   A   H   Y   I   P   P   L   T   F   V   P   V
```

FIGURE 1B

```
        765         774         783         792         801         810
ACG GTC CCC GCC TAC TGG CAG ATC CAC ATG GAG CGT GTG AAG GTG GGC CCA GGG
T   V   P   A   Y   W   Q   I   H   M   E   R   V   K   V   G   P   G

        819         828         837         846         855         864
CTG ACT CTC TGT GCC AAG GGC TGT GCT GCC ATC CTG GAT ACG GGC ACG TCC CTC
L   T   L   C   A   K   G   C   A   A   I   L   D   T   G   T   S   L

        873         882         891         900         909         918
ATC ACA GGA CCC ACT GAG GAG ATC CGG GCC CTG CAT GCA GCC ATT GGG GGA ATC
I   T   G   P   T   E   E   I   R   A   L   H   A   A   I   G   G   I

        927         936         945         954         963         972
CCC TTG CTG GCT GGG GAG TAC ATC ATC CTG TGC TCG GAA ATC CCA AAG CTC CCC
P   L   L   A   G   E   Y   I   I   L   C   S   E   I   P   K   L   P

        981         990         999        1008        1017        1026
GCA GTC TCC TTC CTT CTT GGG GGG GTC TGG TTT AAC CTC ACG GCC CAT GAT TAC
A   V   S   F   L   L   G   G   V   W   F   N   L   T   A   H   D   Y

       1035        1044        1053        1062        1071        1080
GTC ATC CAG ACT ACT CGA AAT GGC GTC CGC CTC TGC TTG TCC GGT TTC CAG GCC
V   I   Q   T   T   R   N   G   V   R   L   C   L   S   G   F   Q   A

       1089        1098        1107        1116        1125        1134
CTG GAT GTC CCT CCG CCT GCA GGG CCC TTC TGG ATC CTC GGT GAC GTC TTC TTG
L   D   V   P   P   P   A   G   P   F   W   I   L   G   D   V   F   L
```

FIGURE 1C

```
        1143          1152          1161          1170          1179          1188
GGG ACG TAT GTG GCC GTC TTC GAC CGC GGG GAC ATG AAG AGC AGC GCC CGG GTG
G   T   Y   V   A   V   F   D   R   G   D   M   K   S   S   A   R   V

        1197          1206          1215          1224          1233          1242
GGC CTG GCG CGC GCT CGC ACT CGC GGA GCG GAC CTC GGA TGG GGA GAG ACT GCG
G   L   A   R   A   R   T   R   G   A   D   L   G   W   G   E   T   A

        1251          1260
CAG GCG CAG TTC CCC GGG TGA  3'
Q   A   Q   F   P   G
```

FIGURE 1D

```
                9          18          27          36          45          54
5' GAA TTC CGG GTC GAC CAC GCG TCC GCA GCA ATG TCT CCA CCA CTG CTG CTG CTA
                                           M   S   P   P   L   L   L   L

               63          72          81          90          99         108
   CCC TTG CTG CTG CTG CTG CCT CTG CTG AAT GTG GAG CCT GCT GGG GCC ACA CTG
   P   L   L   L   L   L   P   L   L   N   V   E   P   A   G   A   T   L

              117         126         135         144         153         162
   ATC CGG ATC CCT CTT CGT CAA GTC CAC CCT GGA CGC AGG ACC CTG AAC CTA CTG
   I   R   I   P   L   R   Q   V   H   P   G   R   R   T   L   N   L   L

              171         180         189         198         207         216
   AGG GGA TGG GGA AAA CCA GCA GAG CTC CCC AAG TTG GGG GCC CCA TCC CCT GGG
   R   G   W   G   K   P   A   E   L   P   K   L   G   A   P   S   P   G

              225         234         243         252         261         270
   GAC AAG CCT GCC TCG GTA CCT CTC TCC AAA TTC CTG GAT GCC CAG TAT TTT GGG
   D   K   P   A   S   V   P   L   S   K   F   L   D   A   Q   Y   F   G

              279         288         297         306         315         324
   GAA ATT GGG CTG GGA ACG CCT CCA CAA AAC TTC ACT GTT GCC TTT GAC ACT GGC
   E   I   G   L   G   T   P   P   Q   N   F   T   V   A   F   D   T   G

              333         342         351         360         369         378
   TCC TCC AAT CTC TGG GTC CCG TCC AGG AGA TGC CAC TTC TTC AGT GTG CCC TGC
   S   S   N   L   W   V   P   S   R   R   C   H   F   F   S   V   P   C
```

FIGURE 2A 387 396 405 414 423 432
TGG TTC CAC CAC CGC TTC AAT CCC AAT GCC TCC AGC TCC TTC AAG CCC AGT GGG
W F H H R F N P N A S S S F K P S G 441 450 459 468 477 486
ACC AAG TTT GCC ATT CAG TAT GGA ACT GGG CGG GTA GAT GGA ATC CTG AGT GAG
T K F A I Q Y G T G R V D G I L S E 495 504 513 522 531 540
GAC AAG CTG ACT ATT GGT GGA ATC AAG GGT GCA TCC GTG ATT TTC GGG GAA GCT
D K L T I G G I K G A S V I F G E A 549 558 567 576 585 594
CTG TGG GAA TCC AGC CTG GTC TTC ACT GTT TCC CGC CCC GAT GGG ATA TTG GGC
L W E S S L V F T V S R P D G I L G 603 612 621 630 639 648
CTC GGT TTT CCC ATT CTG TCT GTG GAA GGA GTT CGG CCC CCG CTG GAT GTA CTG
L G F P I L S V E G V R P P L D V L 657 666 675 684 693 702
GTG GAG CAG GGG CTA TTG GAT AAG CCT GTC TTC TCC TTT TAC TTC AAC AGG GAC
V E Q G L L D K P V F S F Y F N R D 711 720 729 738 747 756
CCT GAA GTG GCT GAT GGA GGA GAG CTG GTC CTG GGG GGC TCA GAC CCG GCA CAC
P E V A D G G E L V L G G S D P A H

FIGURE 2B

```
        765         774         783         792         801         810
TAC ATC CCA CCC CTC ACC TTC GTG CCA GTC ACA GTC CCC GCC TAC TGG CAG ATC
Y   I   P   P   L   T   F   V   P   V   T   V   P   A   Y   W   Q   I

        819         828         837         846         855         864
CAC ATG GAG CGT GTG AAG GTG GGC TCA CGG CTG ACT CTC TGT GCC CAG GGC TGT
H   M   E   R   V   K   V   G   S   R   L   T   L   C   A   Q   G   C

        873         882         891         900         909         918
GCT GCC ATC CTG GAT ACA GGC ACA CCT GTC ATC GTA GGA CCC ACT GAG GAG ATC
A   A   I   L   D   T   G   T   P   V   I   V   G   P   T   E   E   I

        927         936         945         954         963         972
CGG GCC CTG CAT GCA GCC ATT GGG GGA ATC CCC TTG CTG GCT GGG GAG TAC ATC
R   A   L   H   A   A   I   G   G   I   P   L   L   A   G   E   Y   I

        981         990         999        1008        1017        1026
ATC CGG TGC TCA GAA ATC CCA AAG CTC CCC GCA GTC TCA CTC CTC ATT GGG GGG
I   R   C   S   E   I   P   K   L   P   A   V   S   L   L   I   G   G

       1035        1044        1053        1062        1071        1080
GTC TGG TTT AAT CTC ACG GCC CAG GAT TAC GTC ATC CAG TTT GCT CAG GGT GAC
V   W   F   N   L   T   A   Q   D   Y   V   I   Q   F   A   Q   G   D

       1089        1098        1107        1116        1125        1134
GTC CGC CTC TGC TTG TCC GGC TTC CGG GCC TTG GAC ATC GCT TCG CCT CCA GTA
V   R   L   C   L   S   G   F   R   A   L   D   I   A   S   P   P   V
```

FIGURE 2C

```
        1143             1152             1161             1170             1179             1188
CCT GTG TGG ATC CTC GGC GAC GTT TTC TTG GGG GCG TAT GTG ACC GTC TTC GAC
P   V   W   I   L   G   D   V   F   L   G   A   Y   V   T   V   F   D

        1197             1206             1215             1224             1233             1242
CGC GGG GAC ATG AAG AGC GGC GCA CGA GTG GGA CTG GCG CGC GCT CGC CCT CGC
R   G   D   M   K   S   G   A   R   V   G   L   A   R   A   R   P   R

        1251             1260             1269             1278             1287             1296
GGA GCG GAC CTG GGA AGG CGC GAG ACC GCG CAG GCG CAG TAC CGC GGG TGC CGC
G   A   D   L   G   R   R   E   T   A   Q   A   Q   Y   R   G   C   R

        1305             1314             1323
CCA GGT GAT GCG CAT GCG CAC CGG GTA GCA GAG 3'
P   G   D   A   H   A   H   R   V   A   E
```

FIGURE 2D

```
1   M S P P P L L Q P L L L L L P L L N V E P S G A T L I R I P  NHAP-1
1   M S P P L L L L P L L L L L P L L N V E P A G A T L I R I P  NHAP-2
1   M S P L L L - - - L L L C L L L G N L E P E E A K L I R V P  GI1906810

31  L H R V Q P G R R T L N L L R G W R E P A E L P K L G A P S  NHAP-1
31  L R Q V H P G R R T L N L L R G W G K P A E L P K L G A P S  NHAP-2
28  L Q R I H L G H R I L N P L N G W E Q L A E L S R - - T S T  GI1906810

61  P G D K P I F V P L S N Y R D V Q Y F G E I G L G T P P Q N  NHAP1
61  P G D K P A S V P L S K F L D A Q Y F G E I G L G T P P Q N  NHAP-2
56  S G G N P S F V P L S K F M N T Q Y F G T I G L G T P P Q N  GI1906810

91  F T V A F D T G S S N L W V P S R R C H F F S V P C W L H H  NHAP-1
91  F T V A F D T G S S N L W V P S R R C H F F S V P C W F H H  NHAP-2
86  F T V V F D T G S S N L W V P S T R C H F F S L A C W F H H  GI1906810

121 R F D P K A S S S F Q A N G T K F A I Q Y G T G R V D G I L  NHAP-1
121 R F N P N A S S S F K P S G T K F A I Q Y G T G R V D G I L  NHAP-2
116 R F N P K A S S S F R P N G T K F A I Q Y G T G R L S G I L  GI1906810

151 S E D K L T I G G I K G A S V I F G E A L W E P S L V F A F  NHAP-1
151 S E D K L T I G G I K G A S V I F G E A L W E S S L V F T V  NHAP-2
146 S Q D N L T I G G I H D A F V T F G E A L W E P S L I F A L  GI1906810
```

FIGURE 3A

```
181 A H F D G I L G L G F P I L S V E G V R P P M D V L V E Q G NHAP-1
181 S R P D G I L G L G F P I L S V E G V R P P L D V L V E Q G NHAP-2
176 A H F D G I L G L G F P T L A V G G V Q P P L D A M V E Q G GI1906810

211 L L D K P V F S F Y L N R D P E E P D G G E L V L G G S D P NHAP-1
211 L L D K P V F S F Y F N R D P E V A D G G E L V L G G S D P NHAP-2
206 L L E K P V F S F Y L N R D S E G S D G G E L V L G G S D P GI1906810

241 A H Y I P P L T F V P V T V P A Y W Q I H M E R V K V G P G NHAP-1
241 A H Y I P P L T F V P V T V P A Y W Q I H M E R V K V G S R NHAP-2
236 A H Y V P P L T F I P V T I P A Y W Q V H M E S V K V G T G GI1906810

271 L T L C A K G C A A I L D T G T S L I T G P T E E I R A L H NHAP-1
271 L T L C A Q G C A A I L D T G T P V I V G P T E E I R A L H NHAP-2
266 L S L C A Q G C S A I L D T G T S L I T G P S E E I R A L N GI1906810

301 A A I G G I P L L A G E Y I I L C S E I P K L P A V S F L L NHAP-1
301 A A I G G I P L L A G E Y I I R C S K I P X L P A V S L L I NHAP-2
296 K A I G G Y P F L N G Q Y F I Q C S K T P T L P P V S F H L GI1906810

331 G G V W F N L T A H D Y V I Q T T R N G V R L C L S G F Q A NHAP-1
331 G G V W F N L T A Q D Y V I Q F A Q G D V R L C L S G F R A NHAP-2
326 G G V W F N L T G Q D Y V I K I L Q S D V G L C L L G F Q A GI1906810
```

FIGURE 3B

```
361 L D V P P P A G P F W I L G D V F L G T Y V A V F D R G D M NHAP-1
361 L D I A S P P V P V W I L G D V F L G A Y V T V F D R G D M NHAP-2
356 L D I P K P A G P L W I L G D V F L G P Y V A V F D R G D K GI1906810

391 K S S A R V G L A R A R T R G A D L G W G E T A Q A Q F P G NHAP-1
391 K S G A R V G L A R A R P R G A D L G R R E T A Q A Q Y R G NHAP-2
386 N V G P R V G L A R A Q S R S T D R A E R R T T Q A Q F F K GI1906810

420                                                             NHAP-1
421 C R P G D A H A H R V A E                                   NHAP-2
416 R R P G                                                     GI1906810
```

FIGURE 3C

HUMAN ASPARTIC PROTEASES

This application is a divisional application of U.S. patent application Ser. No. 09/116,641, entitled "Human Aspartic Proteases," filed Jul. 16, 1998 which is a continuation in part of Ser. No. 09/008,271, filed Jan. 16, 1998 now U.S. Pat. No. 6,203,979.

FIELD OF THE INVENTION

This invention relates to nucleic acid and amino acid sequences of aspartic proteases and to the use of these sequences in the diagnosis, treatment, and prevention of respiratory, endocrinological, and immunological disorders, and cancer.

BACKGROUND OF THE INVENTION

Proteolytic processing is an essential component of normal cell growth, differentiation, remodeling, and homeostasis. The cleavage of peptide bonds within cells is necessary for the maturation of precursor proteins to their active form, the removal of signal sequences from targeted proteins, the degradation of incorrectly folded proteins, and the controlled turnover of peptides within the cell. Proteases participate in apoptosis, inflammation, and in tissue remodeling during embryonic development, wound healing, and normal growth. They are necessary components of bacterial, parasitic, and viral invasion and replication within a host. Four principal categories of mammalian proteases have been identified based on active site structure, mechanism of action, and overall three-dimensional structure. (Beynon, R. J. and J. S. Bond (1994) *Proteolytic Enzymes: A Practical Approach*, Oxford University Press, New York, N.Y., pp. 1–5.)

One category is the cysteine proteases involved in diverse cellular processes ranging from the processing of precursor proteins to intracellular degradation of proteins. Cysteine proteases are produced by monocytes, macrophages and other cells of the immune system which migrate to sites of inflammation and in their protective role secrete various molecules to repair damaged tissue. These cells may overproduce the same molecules and cause tissue destruction in certain disorders. The cathepsin family of lysosomal proteases includes the cysteine proteases, including cathepsins B, H, K, L, O2, and S, and the aspartic proteases, including pepsin A, gastricsin, chymosin, renin, and cathepsins D and E. Various members of this endosomal protease family are differentially expressed. Some, such as cathepsin D, have a ubiquitous tissue distribution while others, such as cathepsin L, are found only in monocytes, macrophages, and other cells of the immune system.

The characteristic active site residues of aspartic proteases are a pair of aspartic acid residues, e.g., asp33 and asp213 in penicillopepsin. Aspartic proteases are also called acid proteases because the optimum pH for activity is between 2 and 3. In this pH range, one of the aspartate residues is ionized, the other un-ionized. A potent inhibitor of aspartic proteases is the hexapeptide, pepstatin, which in the transition state resembles the normal substrate.

Abnormal regulation and expression of cathepsins is evident in various inflammatory disease states. In autoimmune diseases such as rheumatoid arthritis, the secretion of the cysteine protease, cathepsin C, degrades collagen, laminin, elastin and other structural proteins found in the extracellular matrix of bones. In cells isolated from inflamed synovia, the mRNA for stromelysin, cytokines, TIMP-1, cathepsin, gelatinase, and other molecules is preferentially expressed. Expression of cathepsins L and D is elevated in synovial tissues from patients with rheumatoid arthritis and osteoarthritis. Cathepsin L expression may also contribute to the influx of mononuclear cells which exacerbates the destruction of the rheumatoid synovium. (Keyszer, G. M. (1995) Arthritis Rheum. 38:976–984.) The increased expression and differential regulation of the cathepsins is linked to the metastatic potential of a variety of cancers and as such is of therapeutic and prognostic interest. (Chambers, A. F. et al. (1993) Crit. Rev. Oncog. 4:95–114.)

The discovery of new aspartic proteases and the polynucleotides encoding then satisfies a need in the art by providing new compositions which are useful in the diagnosis, treatment, and prevention of respiratory, endocrinological, and immunological disorders, and cancer.

SUMMARY OF THE INVENTION

The invention features substantially purified polypeptides, aspartic proteases, referred to collectively as "NHAP" and individually as "NHAP-1" and "NHAP-2." In one aspect, the invention provides a substantially purified polypeptide comprising an amino acid sequence selected from the group consisting of SEQ ID NO:1, SEQ ID NO:3, a fragment of SEQ ID NO:1, and a fragment of SEQ ID NO:3.

The invention further provides a substantially purified variant having at least 90% amino acid identity to the amino acid sequences of SEQ ID NO:1 or SEQ ID NO:3, or to a fragment of either of these sequences. The invention also provides an isolated and purified polynucleotide encoding the polypeptide comprising an amino acid sequence selected from the group consisting of SEQ ID NO:1, SEQ ID NO:3, a fragment of SEQ ID NO:1, and a fragment of SEQ ID NO:3. The invention also includes an isolated and purified polynucleotide variant having at least 70% polynucleotide sequence identity to the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3, as well as an isolated and purified polynucleotide having a sequence which is complementary to the polynucleotide encoding the polypeptide comprising the amino acid sequence selected from the group consisting of SEQ ID NO:1, SEQ ID NO:3, a fragment of SEQ ID NO:1, and a fragment of SEQ ID NO:3.

The invention also provides an isolated and purified polynucleotide comprising a polynucleotide sequence selected from the group consisting of SEQ ID NO:2, SEQ ID NO:4, a fragment of SEQ ID NO:2, and a fragment of SEQ ID NO:4. The invention further provides an isolated and purified polynucleotide variant having at least 70% polynucleotide sequence identity to the polynucleotide sequence comprising a polynucleotide sequence selected from the group consisting of SEQ ID NO:2, SEQ ID NO:4, a fragment of SEQ ID NO:2, and a fragment of SEQ ID NO:4, as well as an isolated and purified polynucleotide having a sequence which is complementary to the polynucleotide comprising a polynucleotide sequence selected from the group consisting of SEQ ID NO:2, SEQ ID NO:4, a fragment of SEQ ID NO:2, and a fragment of SEQ ID NO:4.

The invention further provides an expression vector containing at least a fragment of the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3. In another aspect, the expression vector is contained within a host cell.

The invention also provides a method for producing a polypeptide comprising the amino acid sequence selected from the group consisting of SEQ ID NO:1, SEQ ID NO:3, a fragment of SEQ ID NO:1, and a fragment of SEQ ID NO:3, the method comprising the steps of: (a) culturing the host cell containing an expression vector containing at least a fragment of a polynucleotide encoding the polypeptide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:3, a fragment of SEQ ID NO:1, and a fragment of SEQ ID NO:3 in conjunction with a suitable pharmaceutical carrier.

The invention further includes a purified antibody which binds to a polypeptide comprising the amino acid sequence selected from the group consisting of SEQ ID NO:1, SEQ ID NO:3, a fragment of SEQ ID NO:1, and a fragment of SEQ ID NO:3, as well as a purified agonist and a purified antagonist to the polypeptide.

The invention also provides a method for treating or preventing an endocrinological disorder associated with decreased expression or activity of NHAP, the method comprising administering to a subject in need of such treatment an effective amount of a pharmaceutical composition comprising a substantially purified polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing an endocrinological disorder associated with increased expression or activity of NHAP, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a cancer, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing an immunological disorder, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for treating or preventing a respiratory disorder, the method comprising administering to a subject in need of such treatment an effective amount of an antagonist of the polypeptide having an amino acid sequence selected from the group consisting of SEQ ID NO:1, SEQ ID NO:3, a fragment of SEQ ID NO:1, and a fragment of SEQ ID NO:3.

The invention also provides a method for detecting a polynucleotide encoding the polypeptide comprising the amino acid sequence selected from the group consisting of SEQ ID NO:1, SEQ ID NO:3, a fragment of SEQ ID NO:1, and a fragment of SEQ ID NO:3 in a biological sample containing nucleic acids, the method comprising the steps of: (a) hybridizing the complement of the polynucleotide sequence encoding the polypeptide comprising the amino acid sequence selected from the group consisting of SEQ ID NO:1, SEQ ID NO:3, a fragment of SEQ ID NO:1, and a fragment of SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding the polypeptide in the biological sample. In one aspect, the method further comprises amplifying the polynucleotide prior to hybridization.

BRIEF DESCRIPTION OF THE FIGURES AND TABLES

FIGS. 1A, 1B, 1C, and 1D show the amino acid sequence (SEQ ID NO:1) and nucleic acid sequence (SEQ ID NO:2) of NHAP-1. The alignment was produced using MacDNASIS PRO software (Hitachi Software Engineering Co. Ltd., San Bruno, Calif.).

FIGS. 2A, 2B, 2C, and 2D show the amino acid sequence (SEQ ID NO:3) and nucleic acid sequence (SEQ ID NO:4) of NHAP-2. The alignment was produced using MacDNASIS PRO software FIGS. 3A, 3B, and 3C show the amino acid sequence alignments among NHAP-1 (372637; SEQ ID NO:1), NHAP-2 (2435410; SEQ ID NO:3), and a mouse kidney-derived, aspartic protease-like protein (GI 1906810; SEQ ID NO:10), produced using the multisequence alignment program of LASERGENE software (DNASTAR Inc, Madison Wis.).

Figure 6:
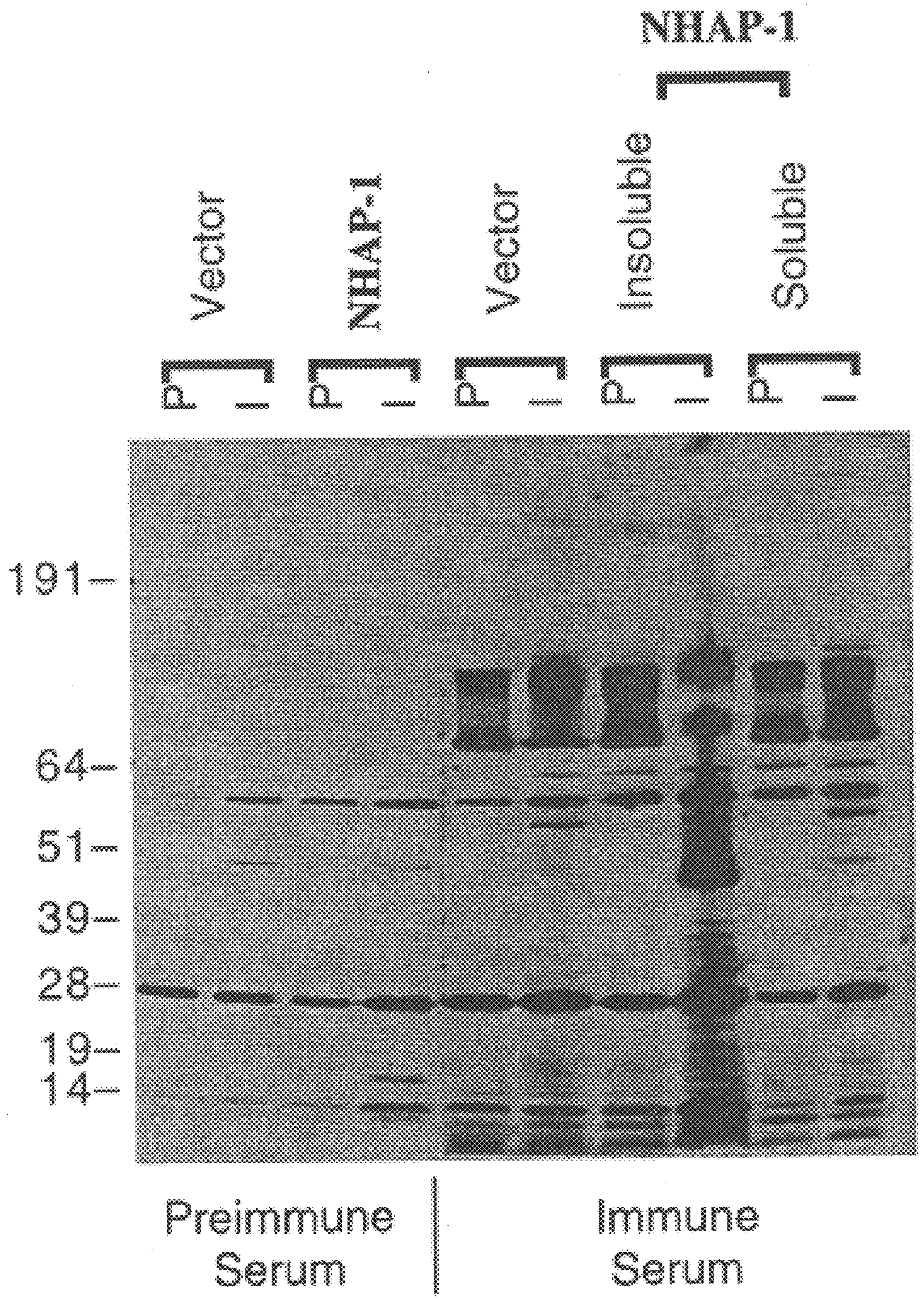

FIG. 6 shows western analysis of recombinant NHAP-1 protein expression in *Escherichia coli*. Competent *E. Coli* strain BL21 (DE3) was transformed with either vector (pET15b) or with NHAP-1 expression construct (pET15b/NHAP-1). Cell lysates from cultures before IPTG induction (P) or after IPTG induction (I) were separated using polyacrylamide gel electrophoresis under reduced denatured conditions, and probed with preimmune and immune serums (IC620).

Table 1 shows the Incyte clone and the associated library in which nucleic acid sequences encoding NHAP were identified, a brief description of the library, and the vector into which each cDNA was cloned.

Table 2 summarizes the databases and tools used to assemble and analyze the sequences of the invention. The first column of Table 2 shows the tool, program, or algorithm; the second column, the database; the third column, a brief description; and the fourth column (where applicable), scores for determining the strength of a match between two sequences (the higher the value, the more homologous).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"NHAP," as used herein, refers to the amino acid sequences, or variant thereof, of substantially purified NHAP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to NHAP, increases or prolongs the duration of the effect of NHAP. Agonists may include proteins, nucleic acids, carbohydrates, or any other molecules which bind to and modulate the effect of NHAP.

An "allelic variant," as this term is used herein, is an alternative form of the gene encoding NHAP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding NHAP, as described herein, include those sequences with deletions, insertions, or substitutions of different nucleotides, resulting in a polynucleotide the same as NHAP or a polypeptide with at least one functional characteristic of NHAP. Included within this definition are polymorphisms which may or may not be readily detectable using a particular oligonucleotide probe of the polynucleotide encoding NHAP, and improper or unexpected hybridization to allelic variants, with a locus other than the normal chromosomal locus for the polynucleotide sequence encoding NHAP. The encoded protein may also be "altered," and may contain deletions, insertions, or substitutions of amino acid residues which produce a silent change and result in a functionally equivalent NHAP. Deliberate amino acid substitutions may be made on the basis of similarity in polarity, charge, solubility, hydrophobicity, hydrophilicity, and/or the amphipathic nature of the residues, as long as the biological or immunological activity of NHAP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of NHAP which are preferably at least 5 to about 15 amino acids in length, most preferably at least 14 amino acids, and which retain some biological activity or immunological activity of NHAP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp.1–5.)

The term "antagonist," as it is used herein, refers to a molecule which, when bound to NHAP, decreases the amount or the duration of the effect of the biological or immunological activity of NHAP. Antagonists may include proteins, nucleic acids, carbohydrates, antibodies, or any other molecules which decrease the effect of NHAP.

As used herein, the term "antibody" refers to intact molecules as well as to fragments thereof, such as Fab, $F(ab')_2$, and Fv fragments, which are capable of binding the epitopic determinant. Antibodies that bind NHAP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic NHAP, or of any oligopeptide thereof, to induce a specific immune response in appropriate animals or cells and to bind with specific antibodies.

The terms "complementary" or "complementarity," as used herein, refer to the natural binding of polynucleotides by base pairing. For example, the sequence "5' A-G-T 3'" binds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding NHAP or fragments of NHAP may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g.,sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR (PE Biosystems, Foster City, Calif.)) in the 5' and/or the 3' direction, and resequenced, or which has been assembled from the overlapping sequences of more than one Incyte Clone using a computer program for fragment assembly, such as the GELVIEW Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding NHAP, by Northern analysis is indicative of the presence of nucleic acids encoding NHAP in a sample, and thereby correlates with expression of the transcript from the polynucleotide encoding NHAP.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Inc., Madison Wis.). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of NHAP. For example, modulation may cause an increase or a decrease in protein activity, binding characteristics, or any other biological, functional, or immunological properties of NHAP.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding NHAP, or fragments thereof, or NHAP itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of NHAP polypeptides, as used herein, refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR Inc).

The term "variant," when used in the context of a polynucleotide sequence, may encompass a polynucleotide sequence related to NHAP. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of two new human aspartic proteases (NHAP), the polynucleotides encoding NHAP, and the use of these compositions for the diagnosis, treatment, or prevention of respiratory, endocrinological, and immunological disorders, and cancer.

Nucleic acids encoding the NHAP-1 and NHAP-2 of the present invention were identified in the following Incyte Clones: (SEQ ID NO:5 through 9) 372637H1 (LUNGNOT02), 1242901H1 (LUNGNOT03), 2222291H1 (LUNGNOT18), 2435410H1 (EOSINOT03), and 2756549H1 (THP1AZS08) using a computer search, e.g., BLAST, for amino acid sequence alignments. The full length cDNA sequence of NHAP-1 (SEQ ID NO:2) was obtained from a human lung cDNA library using the GENETRAPPER method (Life Technologies, Gaithersburg Md.) and oligonucleotides derived from Incyte clone 2756549 (THP1AZS08). The full length cDNA sequence of NHAP-2 (SEQ ID NO:4) was obtained from a human leukocyte cDNA library using the GENETRAPPER method (Life Technologies) and the same oligonucleotides as were used for NHAP-1.

In one embodiment, the invention encompasses a polypeptide comprising the amino acid sequence of SEQ ID NO:1, as shown in FIGS. 1A, 1B, 1C, and 1D. NHAP-1 is 420 amino acids in length and has a potential signal peptide sequence extending from residues M1 to P21. Potential N-glycosylation sites are found at residues N90, N133, and N336. Potential phosphorylation sites are found for casein kinase II at S60 and T338, and for protein kinase C at S106, T143, T346, and S393. Two potential leucine zipper patterns are found beginning at L309 and L316, and a potential cell attachment site is found in the sequence R387GD. Two potential active site aspartate residues, characteristic of aspartic proteases, are found at residues D96 and D283. BLOCKS and PRINTS analyses also identify sequences encompassing the two aspartate residues as characteristic of aspartic proteases. As shown in FIGS. 3A, 3B, and 3C, NHAP-1 has chemical and structural similarity with a mouse aspartic protease-like protein (GI 1906810; SEQ ID NO:10). In particular, NHAP-1 and the mouse aspartic protease-like protein share 69% identity. The two proteins share the signal sequence, the three potential glycosylation sites, and the potential phosphorylations sites found in NHAP-1 at S106, T143, and T338. The two potential active site aspartate residues found in NHAP-1 and NHAP-2, and the surrounding sequences, are also conserved in the mouse protein. The fragment of SEQ ID NO:2 from about nucleotide 160 to about nucleotide 228, which encodes a fragment of SEQ ID NO:1 from about amino acid residue P54 to about amino acid residue V76, is useful, for example, as a hybridization probe.

In another embodiment, the invention encompasses a polypeptide comprising the amino acid sequence of SEQ ID NO:3, as shown in FIGS. 2A, 2B, 2C, and 2D. NHAP-2 is 433 amino acids in length and has a potential signal sequence extending from residues M1 to P21, three potential N-glycosylation sites at N90, N125, and N336, potential phosphorylation sites for cAMP-cGMP-dependent protein kinase at T413, for casein kinase at S60, S181, T338, and T383, for protein kinase C at S106, S129, and T143, and for tyrosine kinase at Y78, and a potential cell attachment site is found in the sequence R387GD. Two potential active site aspartate residues, characteristic of aspartic proteases, are found at residues D96 and D283. BLOCKS and PRINTS analyses also identify sequences encompassing the two aspartate residues as characteristic of aspartic proteases. As shown in FIGS. 3A, 3B and 3C, NHAP-2 has chemical and structural similarity with a mouse aspartic protease- like protein (GI 1906810; SEQ ID NO:10). In particular, NHAP-2 and the mouse aspartic protease-like protein share 69% identity, the two potential glycosylation sites at N90 and N336, and the potential phosphorylations sites found in NHAP-2 at S106, S129, T143 and T338. The two potential active site aspartate residues found in NHAP-2, and their surrounding sequences, are also conserved in the mouse protein. The sequence of SEQ ID NO:4 from about nucleotide 190 to about nucleotide 258, which encodes a fragment of SEQ ID NO:3 from about amino acid residue P54 to about amino acid residue A76, is useful, for example, as a hybridization probe.

Figure 4:
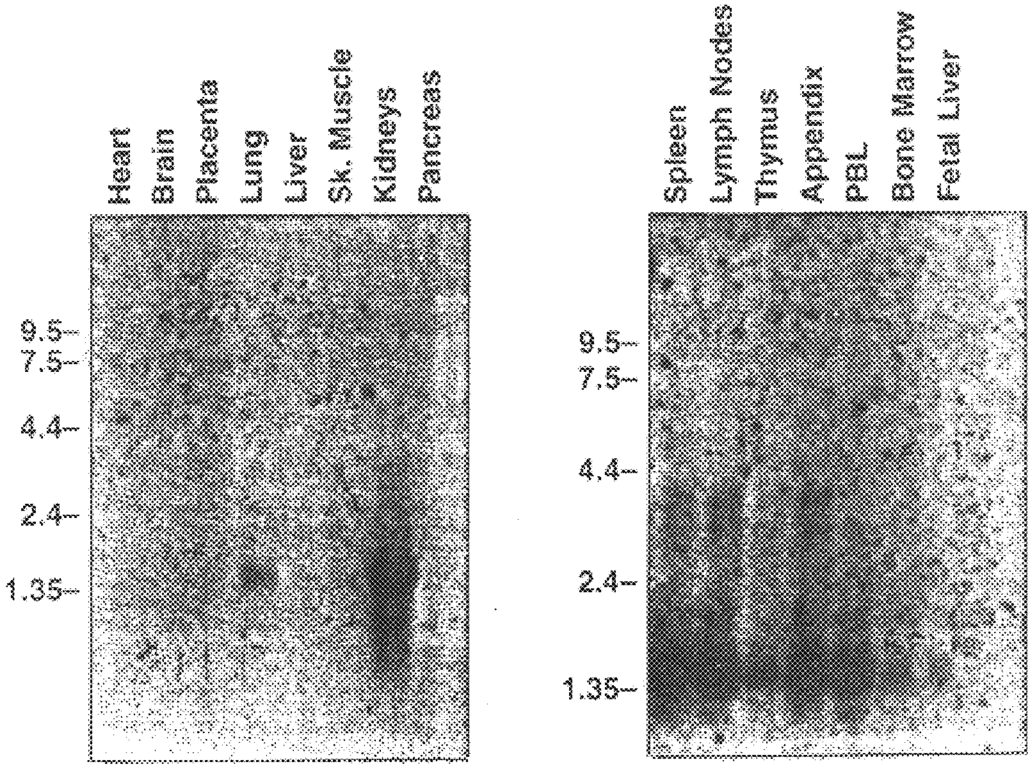
FIG. 4 shows the northern analysis of NHAP-1 and NHAP-2 probed with NHAP-2 cDNA. Tissue blots were obtained from Clontech, Palo Alto, Calif.

Electronic northern analysis shows clones clustered with NHAP expressed in a variety of cDNA libraries at least 59% of which involve cancer and immortalized cell lines, and at least 22% of which involve inflammation and the immune response. Of particular note is the expression of NHAP in lung tissue (37%). Membrane based northern analysis using NHAP-2 cDNA showed the expression of an ~ 1.3 kb RNA species in kidney, lung, and tissues associated with the immune response, including spleen, bone marrow, and peripheral blood leukocytes (FIG. 4). Since the NHAP-2 probe has ~90% homology to NHAP-1, the analysis represents the expression of both NHAP-1 and NHAP-2. Membrane based northern analysis using an oligonucleotide probe specific for NHAP-1 (FIG. 5) showed the expression of the ~1.3 kb RNA species only in lung. Immunocytochemical staining of normal and diseased human tissue samples using NHAP-1 specific rabbit immune serum demonstrated the expression of the protein in pituitary gland, thyroid follicular cells, normal lung alveoli, bronchioloalveolar carcinoma and lung adenocarcinoma.

FIG. 6 shows the western analysis of recombinant NHAP-1 protein expressed in *E. Coli*. NHAP-1 was detected as a band of around 45 kDa using immune, but not preimmune, serum and was found predominantly in IPTG-induced cells containing the NHAP-1 expression construct.

Chromosomal localization studies by FISH analysis revealed that genes encoding NHAP-1 and NHAP-2 were localized to the long arms of chromosome 19, specifically to an area corresponding to band 19q13.3.

The invention also encompasses NHAP variants. A preferred NHAP variant is one which has at least about 80%, more preferably at least about 90%, and most preferably at least about 95% amino acid sequence identity to the NHAP amino acid sequence, and which contains at least one functional or structural characteristic of NHAP.

The invention also encompasses polynucleotides which encode NHAP. In a particular embodiment, the invention encompasses a polynucleotide sequence comprising the sequence of SEQ ID NO:2, which encodes an NHAP. In a further embodiment, the invention encompasses the polynucleotide sequence comprising the sequence of SEQ ID NO:4, which encodes an NHAP.

The invention also encompasses a variant of a polynucleotide sequence encoding NHAP. In particular, such a variant polynucleotide sequence will have at least about 70%, more preferably at least about 80%, and most preferably at least about 95% polynucleotide sequence identity to the polynucleotide sequence encoding NHAP. A particular aspect of the invention encompasses a variant of SEQ ID NO:2 which has at least about 70%, more preferably at least about 80%, and most preferably at least about 95% polynucleotide sequence identity to SEQ ID NO:2. The invention further encompasses a polynucleotide variant of SEQ ID NO:4 having at least about 70%, more preferably at least about 80%, and most preferably at least about 95% polynucleotide sequence identity to SEQ ID NO:4. Any one of the polynucleotide variants described above can encode an amino acid sequence which contains at least one functional or structural characteristic of NHAP.

It will be appreciated by those skilled in the art that as a result of the degeneracy of the genetic code, a multitude of polynucleotide sequences encoding NHAP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring NHAP, and all such variations are to be considered as being specifically disclosed.

Although nucleotide sequences which encode NHAP and its variants are preferably capable of hybridizing to the nucleotide sequence of the naturally occurring NHAP under appropriately selected conditions of stringency, it may be advantageous to produce nucleotide sequences encoding NHAP possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding NHAP and its derivatives without altering the encoded amino acid sequences include the production of RNA transcripts having more desirable properties, such as a greater half-life, than transcripts produced from the naturally occurring sequence.

The invention also encompasses production of DNA sequences which encode NHAP and NHAP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding NHAP or any fragment thereof.

Also encompassed by the invention are polynucleotide sequences that are capable of hybridizing to the claimed polynucleotide sequences, and, in particular, to those shown in SEQ ID NO:2, SEQ ID NO:4, a fragment of SEQ ID NO:2, or a fragment of SEQ ID NO:4 under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing and analysis are well known in the art. The methods may employ such enzymes as the Klenow fragment of DNA polymerase I, SEQUENASE, Taq DNA polymerase and thermostable T7 DNA polymerase (Amersham Pharmacia Biotech (APB), Piscataway N.J.), or combinations of polymerases and proofreading exonucleases, such as those found in the ELONGASE amplification system (Life Technologies, Rockville Md.). Preferably, sequence preparation is automated with machines such as the HYDRA microdispenser (Robbins Scientific, Sunnyvale Calif.), MICROLAB 2200 (Hamilton, Reno Nev.), and the DNA ENGINE thermal cycler (PTC200; MJ Research, Watertown Mass.). Machines used for sequencing include the ABI 3700, 377 or 373 DNA sequencing systems (PE Biosystems), the MEGABACE 1000 DNA sequencing system (APB), and the like. Sequences can be analyzed using computer programs and algorithms well known in the art. (See, e.g., Ausubel, supra, unit 7.7; and Meyers, R. A. (1995) *Molecular Biology and Biotechnology*, Wiley VCH, Inc, New York, N.Y.)

The nucleic acid sequences encoding NHAP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO 4.06 Primer Analysis software (National Biosciences Inc., Plymouth, Minn.) or another appropriate program, to be about 22 to 30 nucleotides in length, to have a GC. content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, PE Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode NHAP may be cloned in recombinant DNA molecules that direct expression of NHAP, or fragments or functional equivalents thereof, in appropriate host cells. Due to the inherent degeneracy of the genetic code, other DNA sequences which encode substantially the same or a functionally equivalent amino acid sequence may be produced and used to express NHAP.

The nucleotide sequences of the present invention can be engineered using methods generally known in the art in order to alter NHAP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding NHAP may be synthesized, in whole or in part, using chemical methods well known in the art. (See, e.g., Caruthers, M. H. et al. (1980) Nucl. Acids Symp. Ser. 7:215–223, and Horn, T. et al. (1980) Nucl. Acids Symp. Ser. 7:225–232.) Alternatively, NHAP itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A peptide synthesizer (PE Biosystems). Additionally, the amino acid sequence of NHAP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active NHAP, the nucleotide sequences encoding NHAP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding NHAP. Such elements may vary in their strength and specificity. Specific initiation signals may also be used to achieve more efficient translation of sequences encoding NHAP. Such signals include the ATG initiation codon and adjacent sequences, e.g. the Kozak sequence. In cases where sequences encoding NHAP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.) Methods which are well known to those skilled in the art may be used to construct expression vectors containing sequences encoding NHAP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding NHAP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding NHAP. For example, when cloning in bacterial systems, inducible promoters, e.g., hybrid lacZ promoter of the PBLUESCRIPT vector (Stratagene, La Jolla Calif.) or PSPORT1 plasmid (Life Technologies), may be used. Ligation of sequences encoding NHAP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of NHAP are needed, e.g. for the production of antibodies, vectors which direct high level expression of NHAP may be used. For example, vectors containing the strong, inducible T5 or T7 bacteriophage promoter may be used.

Yeast expression systems may be used for production of NHAP. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of NHAP. Transcription of sequences encoding NHAP may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding NHAP may be ligated into an adenovirus transcription/translation complex consisting of the late promoter and tripartite leader sequence. Insertion in a non-essential E1 or E3 region of the viral genome may be used to obtain infective virus which expresses NHAP in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of NHAP in cell lines is preferred. For example, sequences encoding NHAP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in $tk^-$ or $apr^-$ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 25 85:8047–8051.) Visible markers, e.g., anthocyanins, green fluorescent proteins (GFP) (Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding NHAP is inserted within a marker gene sequence, transformed cells containing sequences encoding NHAP can be identified by the absence of marker gene function. Alternatively, a marker gene can be placed in tandem with a sequence encoding NHAP under the control of a single promoter. Expression of the marker gene in response to induction or selection usually indicates expression of the tandem gene as well.

In general, host cells that contain the nucleic acid sequence encoding NHAP and that express NHAP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of NHAP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on NHAP is preferred, but a competitive binding assay may be employed. These and other assays are well known in the art. (See, e.g., Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding NHAP include oligolabeling, nick translation, end-labeling, or PCR amplification using a labeled nucleotide. Alternatively, the sequences encoding NHAP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding NHAP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode NHAP may be designed to contain signal sequences which direct secretion of NHAP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding NHAP may be ligated to a heterologous sequence resulting in translation of a fusion protein in any of the aforementioned host systems. For example, a chimeric NHAP protein containing a heterologous moiety that can be recognized by a commercially available antibody may facilitate the screening of peptide libraries for inhibitors of NHAP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the NHAP encoding sequence and the heterologous protein sequence, so that NHAP may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled NHAP may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of NHAP may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A peptide synthesizer (PE Biosystems). Various fragments of NHAP may be synthesized separately and then combined to produce the full length molecule.

Therapeutics

Chemical and structural similarity, e.g., in the context of sequences and motifs, exists between NHAP and an aspartic protease-like protein from mouse (GI 1906890). In addition, NHAP is expressed in endocrine tissues, cancer, inflammation and the immune response, and respiratory disorders. Therefore, NHAP appears to play a role in respiratory, endocrinological, and immunological disorders, and cancer.

Therefore, in one embodiment, NHAP or a fragment or derivative thereof may be administered to a subject to treat or prevent an endocrinological disorder associated with decreased expression or activity of NHAP. Such disorders can include, but are not limited to, disorders associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism; and disorders associated with hypothyroidism including goiter, myxedema, acute thyroiditis associated with bacterial infection, subacute thyroiditis associated with viral infection, autoimmune thyroiditis (Hashimoto's disease), and cretinism.

In another embodiment, a vector capable of expressing NHAP or a fragment or derivative thereof may be administered to a subject to treat or prevent an endocrinological disorder including, but not limited to, those described above.

In a further embodiment, a pharmaceutical composition comprising a substantially purified NHAP in conjunction with a suitable pharmaceutical carrier may be administered to a subject to treat or prevent an endocrinological disorder including, but not limited to, those provided above.

In still another embodiment, an agonist which modulates the activity of NHAP may be administered to a subject to treat or prevent an endocrinological disorder including, but not limited to, those listed above.

In a further embodiment, an antagonist of NHAP may be administered to a subject to treat or prevent an endocrinological disorder associated with increased expression or activity of NHAP. Such disorders can include, but are not limited to, disorders associated with hyperpituitarism including acromegaly, giantism, and syndrome of inappropriate antidiuretic hormone (ADH) secretion (SIADH); disorders associated with hyperthyroidism including thyrotoxicosis and its various forms, Grave's disease, pretibial myxedema, toxic multinodular goiter, thyroid carcinoma, and Plummer's disease; and disorders associated with hyperparathyroidism including Conn disease (chronic hypercalemia). In one aspect, an antibody which specifically binds NHAP may be used directly as an antagonist or indirectly as a targeting or delivery mechanism for bringing a pharmaceutical agent to cells or tissue which express NHAP.

In an additional embodiment, a vector expressing the complement of the polynucleotide encoding NHAP may be administered to a subject to treat or prevent an endocrinological disorder including, but not limited to, those described above.

In a further embodiment, an antagonist of NHAP may be administered to a subject to treat or prevent a respiratory disorder. Such disorders can include, but are not limited to, allergy, asthma, acute and chronic inflammatory lung diseases, Adult Respiratory Distress Syndrome (ARDS), emphysema, pulmonary congestion and edema, Chronic Obstructive Pulmonary Disease (COPD), interstitial lung diseases, and lung cancers.

In an additional embodiment, a vector expressing the complement of the polynucleotide encoding NHAP may be administered to a subject to treat or prevent a respiratory disorder including, but not limited to, those described above.

In a further embodiment, an antagonist of NHAP may be administered to a subject to treat or prevent a cancer. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In an additional embodiment, a vector expressing the complement of the polynucleotide encoding NHAP may be administered to a subject to treat or prevent a cancer including, but not limited to, those described above.

In a further embodiment, an antagonist of NHAP may be administered to a subject to treat or prevent an immunological disorder. Such disorders may include, but are not limited to, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In an additional embodiment, a vector expressing the complement of the polynucleotide encoding NHAP may be administered to a subject to treat or prevent an immunological disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of NHAP may be produced using methods which are generally known in the art. In particular, purified NHAP may be used to produce antibodies or to screen libraries of pharmaceutical agents to identify those which specifically bind NHAP. Antibodies to NHAP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of polyclonal antibodies, various hosts including goats, rabbits, rats, mice, humans, and others may be immunized by injection with NHAP or with any fragment or oligopeptide thereof which has immunogenic properties. Rats and mice are preferred hosts for downstream applications involving monoclonal antibody production. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable. (For review of methods for antibody production and analysis, see, e.g., Harlow, E. and Lane, D. (1988) *Antibodies: A Laboratory Manual*, Cold Spring Harbor Laboratory, Cold Spring Harbor, N.Y.)

It is preferred that the oligopeptides, peptides, or fragments used to induce antibodies to NHAP have an amino acid sequence consisting of at least about 5 amino acids, and, more preferably, of at least about 14 amino acids. It is also preferable that these oligopeptides, peptides, or fragments are identical to a portion of the amino acid sequence of the natural protein and contain the entire amino acid sequence of a small, naturally occurring molecule. Short stretches of NHAP amino acids may be fused with those of another protein, such as KLH, and antibodies to the chimeric molecule may be produced.

Monoclonal antibodies to NHAP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce NHAP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for NHAP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity and minimal cross-reactivity. Numerous protocols for competitive binding or immunoradiometric assays using either polyclonal or monoclonal antibodies with established specificities are well known in the art. Such immunoassays typically involve the measurement of complex formation between NHAP and its specific antibody. A two-site, monoclonal-based immunoassay utilizing monoclonal antibodies reactive to two non-interfering NHAP epitopes is preferred, but a competitive binding assay may also be employed. (Maddox, supra.)

Various methods such as Scatchard analysis in conjunction with radioimmunoassay techniques may be used to assess the affinity of antibodies for NHAP. Affinity is expressed as an association constant, $K_a$, which is defined as the molar concentration of NHAP-antibody complex divided by the molar concentrations of free antigen and free antibody under equilibrium conditions. The $K_a$ determined for a preparation of polyclonal antibodies, which are heterogeneous in their affinities for multiple NHAP epitopes, represents the average affinity, or avidity, of the antibodies for NHAP. The $K_a$ determined for a preparation of monoclonal antibodies, which are monospecific for a particular NHAP epitope, represents a true measure of affinity. High-affinity antibody preparations with $K_a$ ranging from about $10^9$ to $10^{12}$ L/mole are preferred for use in immunoassays in which the NHAP-antibody complex must withstand rigorous manipulations. Low-affinity antibody preparations with $K_a$ ranging from about $10^6$ to $10^7$ L/mole are preferred for use in immunopurification and similar procedures which ultimately require dissociation of NHAP, preferably in active form, from the antibody. (Catty, D. (1988) *Antibodies, Volume I: A Practical Approach*, IRL Press, Washington, D.C.; and Liddell, J. E. and Cryer, A. (1991) A *Practical Guide to Monoclonal Antibodies*, John Wiley & Sons, New York, N.Y.)

The titre and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of NHAP-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding NHAP, or any fragment or complement thereof, may be used for therapeutic purposes. In one aspect, the complement of the polynucleotide encoding NHAP may be used in situations in which it would be desirable to block the transcription of the mRNA. In particular, cells may be transformed with sequences complementary to polynucleotides encoding NHAP. Thus, complementary molecules or fragments may be used to modulate NHAP activity, or to achieve regulation of gene function. Such technology is now well known in the art, and sense or antisense oligonucleotides or larger fragments can be designed from various locations along the coding or control regions of sequences encoding NHAP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding NHAP. (See, e.g., Sambrook, supra; and Ausubel, supra.)

Genes encoding NHAP can be turned off by transforming a cell or tissue with expression vectors which express high levels of a polynucleotide, or fragment thereof, encoding NHAP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding NHAP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding NHAP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding NHAP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of NHAP, antibodies to NHAP, and mimetics, agonists, antagonists, or inhibitors of NHAP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range 4.5 to 5.5, that is combined with buffer prior to use.

After pharmaceutical compositions have been prepared, they can be placed in an appropriate container and labeled for treatment of an indicated condition. For administration of NHAP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example NHAP or fragments thereof, antibodies of NHAP, and agonists, antagonists or inhibitors of NHAP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind NHAP may be used for the diagnosis of disorders characterized by expression of NHAP, or in assays to monitor patients being treated with NHAP or agonists, antagonists, or inhibitors of NHAP. Antibodies useful for diagnostic purposes may be prepared in the same manner as described above for therapeutics. Diagnostic assays for NHAP include methods which utilize the antibody and a label to detect NHAP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring NHAP, including ELISAs, RIAs, and FACS, are known in the art and provide a basis for diagnosing altered or abnormal levels of NHAP expression. Normal or standard values for NHAP expression are established by combining body fluids or cell extracts taken from normal mammalian subjects, preferably human, with antibody to NHAP under conditions suitable for complex formation. The amount of standard complex formation may be quantitated by various methods, preferably by photometric means. Quantities of NHAP expressed in subject samples, control and disease, from biopsied tissues are compared with the standard values. Deviation between standard and subject values establishes the parameters for diagnosing disease.

In another embodiment of the invention, the polynucleotides encoding NHAP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of NHAP may be correlated with disease. The diagnostic assay may be used to determine absence, presence, and excess expression of NHAP, and to monitor regulation of NHAP levels during therapeutic intervention.

In one aspect, hybridization with PCR probes which are capable of detecting polynucleotide sequences, including genomic sequences, encoding NHAP or closely related molecules may be used to identify nucleic acid sequences which encode NHAP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding NHAP, allelic variants, or related sequences.

Probes may also be used for the detection of related sequences, and should preferably have at least 50% sequence identity to any of the NHAP encoding sequences. The hybridization probes of the subject invention may be DNA or RNA and may be derived from the sequence of SEQ ID NO:2, SEQ ID NO:4 or from genomic sequences including promoters, enhancers, and introns of the NHAP gene.

Means for producing specific hybridization probes for DNAs encoding NHAP include the cloning of polynucleotide sequences encoding NHAP or NHAP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding NHAP may be used for the diagnosis of a disorder associated with expression of NHAP. Examples of such a disorder include, but are not limited to, endocrinological disorders such as disorders associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism; hyperpituitarism including acromegaly, giantism, and syndrome of inappropriate antidiuretic hormone (ADH) secretion (SIADH); and disorders associated with hypothyroidism including goiter, myxedema, acute thyroiditis associated with bacterial infection, subacute thyroiditis associated with viral infection, autoimmune thyroiditis (Hashimoto's disease), and cretinism; disorders associated with hyperthyroidism including thyrotoxicosis and its various forms, Grave's disease, pretibial myxedema, toxic multinodular goiter, thyroid carcinoma, and Plummer's disease; and disorders associated with hyperparathyroidism including Conn disease (chronic hypercalemia); respiratory disorders such as allergy, asthma, acute and chronic inflammatory lung diseases, ARDS, emphysema, pulmonary congestion and edema, COPD, interstitial lung diseases, and lung cancers; cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and immunological disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. The polynucleotide sequences encoding NHAP may be used in Southern or Northern analysis, dot blot, or other membrane-based technologies; in PCR technologies; in dipstick, pin, and ELISA assays; and in microarrays utilizing fluids or tissues from patients to detect altered NHAP expression. Such qualitative or quantitative methods are well known in the art.

In a particular aspect, the nucleotide sequences encoding NHAP may be useful in assays that detect the presence of associated disorders, particularly those mentioned above. The nucleotide sequences encoding NHAP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding NHAP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of NHAP, a normal or standard profile for expression is established. This may be accomplished by combining body fluids or cell extracts taken from normal subjects, either animal or human, with a sequence, or a fragment thereof, encoding NHAP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding NHAP may involve the use of PCR. These oligomers may be chemically synthesized, generated enzymatically, or produced in vitro. Oligomers will preferably contain a fragment of a polynucleotide encoding NHAP, or a fragment of a polynucleotide complementary to the polynucleotide encoding NHAP, and will be employed under optimized conditions for identification of a specific gene or condition. Oligomers may also be employed under less stringent conditions for detection or quantitation of closely related DNA or RNA sequences.

Methods which may also be used to quantitate the expression of NHAP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding NHAP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding NHAP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) *Nature* 336:577–580.) The nucleotide sequence of the subject invention may also be used to detect differences in the chromosomal location due to translocation, inversion, etc., among normal, carrier, or affected individuals.

In another embodiment of the invention, NHAP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between NHAP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with NHAP, or fragments thereof, and washed. Bound NHAP is then detected by methods well known in the art. Purified NHAP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding NHAP specifically compete with a test compound for binding NHAP. In this manner, antibodies can be used to detect the presence of any peptide which shares one or more antigenic determinants with NHAP.

In additional embodiments, the nucleotide sequences which encode NHAP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. Construction of cDNA Libraries

RNA was purchased from Clontech (Palo Alto, Calif.) or isolated at Incyte from tissues described in Table 1. The tissue was homogenized and lysed in guanidinium isothiocyanate, and the lysate was centrifuged over a CsCl cushion. Alternatively, the tissue was homogenized and lysed in phenol or a suitable mixture of denaturants such as TRIZOL reagent (Life Technologies), a monophasic solution of phenol and guanidine isothiocyanate, and the lysate was extracted with chloroform (1:5 v/v). RNA was precipitated from lysates with either isopropanol or sodium acetate and ethanol. Alternatively, RNA was purified from lysates by preparative agarose gel electrophoresis and recovered from Whatman P81 paper (Whatman, Lexington, Mass.). Phenol extraction and precipitation of RNA were repeated as necessary to increase RNA purity, and RNA was maintained in RNase-free solutions. In some cases, RNA was treated with DNase. For most libraries, poly(A+) RNA was isolated using oligo d(T)-coupled paramagnetic particles (Promega, Madison, Wis.), Oligotex resin, or the OLIGOTEX kit (Qiagen, Valencia Calif.). Alternatively, RNA was isolated directly from tissue lysates using the RNA Isolation kit (Stratagene) or the Ambion PolyA Quick kit (Ambion, Austin, Tex.).

RNA was used for cDNA synthesis and construction of the cDNA libraries according to procedures recommended in the UNIZAP vector (Stratagene, La Jolla, Calif.) or SUPERSCRIPT plasmid system (Life Technologies), both of which are based on methods well known in the art (Ausubel, 1997, units 5.1–6.6). Alternatively, cDNA libraries were constructed by Stratagene using RNA provided by Incyte. Reverse transcription was initiated using oligo d(T) or random primers. Synthetic oligonucleotide adapters were ligated to double stranded cDNA, and cDNA was digested with an appropriate restriction enzyme(s). For most libraries, cDNA was size-selected (300–1000 bp) using SEPHACRYL S1000 or SEPHAROSE CL-2B or CL4B column chromatography (Amersham Pharmacia Biotech) or preparative agarose gel electrophoresis. cDNAs were ligated into compatible restriction enzyme sites of the polylinker of a suitable plasmid, e.g., pBluescript (Stratagene), PSPORT1 (Life Technologies), pINCY (Incyte Genomics Inc, Palo Alto, Calif.). pINCY was amplified in JM109 cells and purified using the QIAQUICK column (QIAGEN Inc). Recombinant plasmids were transformed into competent *E. coli* cells, e.g., XL1-Blue, XL1-BlueMRF, or SOLR (Stratagene) or DH5α, DH10B, or ELECTROMAX DH10B cells (Life Technologies).

II. Isolation of cDNA Clones

Plasmids were recovered from host cells by in vivo excision (UNIZAP vector system, Stratagene) or by cell lysis. Plasmids were purified using the MINIPREP kit (Edge Biosystems, Gaithersburg Md.); QIAwell-8 Plasmid, QIAwell PLUS DNA, or QIAwell ULTRA DNA purification systems; or REAL Prep 96 plasmid kit (QIAGEN Inc) using the recommended protocol. Following precipitation, plasmids were resuspended in 0.1 ml of distilled water and stored, with or without lyophilization, at 4° C.

Alternatively, plasmid DNA was amplified from host cell lysates using direct link PCR (Rao, V. B. (1994) Anal. Biochem. 216:1–14) in a high-throughput format. Host cell lysis and thermal cycling steps were carried out in a single reaction mixture. Samples were processed and stored in 384-well plates (Genetix Ltd, Christchurch UK) and concentration of amplified plasmid DNA was quantified fluorometrically using Pico Green Dye (Molecular Probes, Eugene Oreg.) and a Fluoroscan II fluorescence scanner (Labsystems Oy, Helsinki, Finland).

III. Sequencing and Analysis

The cDNAs were prepared for sequencing using either an ABI CATALYST 800 (PE Biosystems) or a Hamilton MICRO LAB 2200 (Hamilton, Reno, Nev.) in combination with the DNA ENGINE thermal cyclers (MJ Research). The cDNAs were sequenced by the method of Sanger and Coulson (1975; J Mol Biol 94:441–448) using an ABI PRISM 377 sequencing system (PE Biosystems). Alternatively, cDNAs were prepared and sequenced using solutions and dyes from Amersham Pharmacia Biotech. Reading frame was determined using standard methods (Ausubel, supra).

The nucleotide sequences and/or amino acid sequences of the Sequence Listing were queried against databases such as GenBank primate (pri), rodent (rod), mammalian (mamp), vertebrate (vrtp), and eukaryote (eukp) databases, SwissProt, BLOCKS, and other databases which contain previously identified and annotated motifs and sequences. Algorithms such as Smith Waterman which deal with primary sequence patterns and secondary structure gap penalties (Smith, T. et al. (1992) Protein Engineering 5:35–51) and programs and algorithms such as BLAST (Basic Local Alignment Search Tool; Altschul, S. F. (1993) J. Mol. Evol 36:290–300; and Altschul et al. (1990) J. Mol. Biol. 215:403–410), and HMM (Hidden Markov Models; Eddy, S. R. (1996) Cur. Opin. Str. Biol. 6:361–365 and Sonnhammer, E. L. L. et al. (1997) Proteins 28:405–420) were used to assemble and analyze nucleotide and amino acid sequences. The databases, programs, algorithms, methods and tools are available, well known in the art, and described in Ausubel (supra, unit 7.7), in Meyers, R. A. (1995; *Molecular Biology and Biotechnology*, Wiley VCH, Inc, New York N.Y., p 856–853), in documentation provided with software (Genetics Computer Group (GCG), Madison Wis.), and on the world wide web (www). Two comprehensive websites which list, describe, and/or link many of the databases and tools are: 1) the www resource in practical sequence analysis (http://genome.wustl.edu/), and 2) the bibliography of computational gene recognition (http://linkage.rockefeller.edu/wli/gene/programs.html). For example, the first website links PFAM as a database (http://genome.wustl.edu/Pfam/) and as an HMM search tool (http://genome.wustl.edu/eddy/cgi-bin/hmm_page.cgi). Table 2 summarizes the databases and tools used herein. The first column of Table 2 shows the tool, program, or algorithm; the second column, the database; the third column, a brief description; and the fourth column (where applicable), scores for determining the strength of a match between two sequences (the higher the value, the more homologous).

IV. Cloning of Full Length NHAP

The GENETRAPPER cDNA Positive Selection System kit (Life Technologies) was employed to isolate full length cDNA clones of NHAP-1 and NHAP-2. Following the manufacturer's instructions, oligonucleotides were designed based on partial nucleic acid sequences from Incyte clone 2756549, biotinylated at the 3' end, and hybridized to single stranded DNA from plasmid cDNA libraries of human lung (Cat. No. 10424-018, Life Technologies) and human leukocytes (Cat. No. 10421-014, Life Technologies). Five cDNA clones; gt83, gt86, gt97, gt88, and gt91 were isolated from lung cDNA library, and five cDNA clones; gt4, gt22, gt49, gt53, and gt90 were isolated from the leukocyte library. Sequencing revealed that the clones isolated from the lung library were identical in nucleic acid sequence to Incyte clones 372637 and 1242901 and to the gene subsequently named NHAP-1 (HUPM-4 in the prior application). However, the clones isolated from the lung library differed in nucleic acid sequences from those isolated from the leukocyte library and from Incyte clones 2435410 and 2756549. Thus two genes were identified and were subsequently named NHAP-1 and NHAP-2. NHAP-1 encompasses cDNA clones gt83, gt86, gt97, gt88, gt91, Incyte clone 372637 and 1242901. NHAP-2 encompasses cDNA clones gt4, gt22, gt49, gt53, gt90 and Incyte clones 2435410 and 2756549. Sequence homology analysis showed 89% nucleic acid identity between NHAP-1 and NHAP-2.

V. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Figure 5:
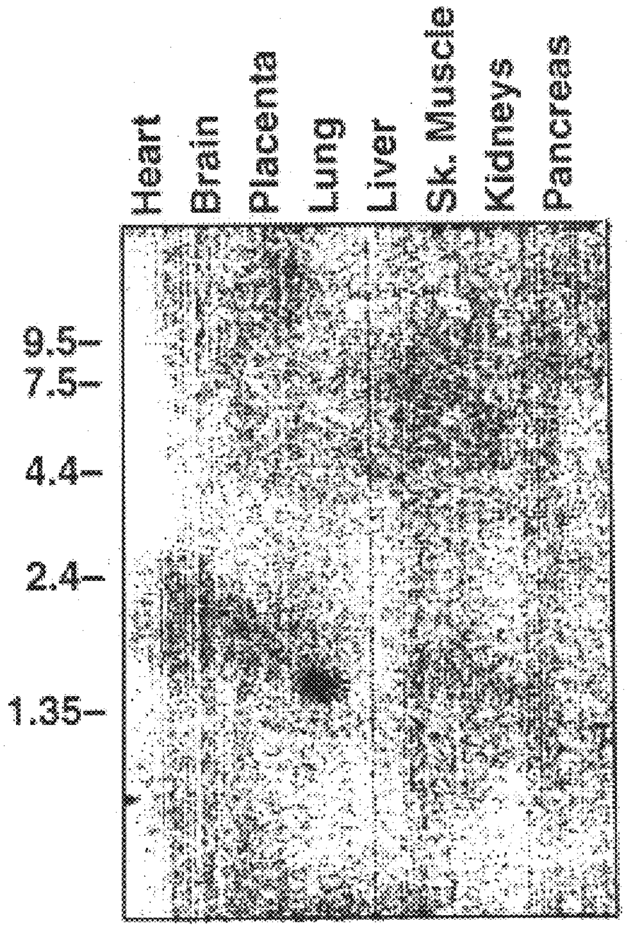
FIG. 5 shows the northern analysis of NHAP-1 probed with NHAP-1-specific oligonucleotide using the same tissue blots as in FIG. 4.

Membrane-based northern analysis was performed on RNA samples from a variety of human tissues using Multiple Tissue Northern Blots (Clontech, Palo Alto, Calif.) probed with NHAP-2 cDNA. The probe was labeled with $^{33}P$ using the random primer labeling method with the HIGH PRIMER DNA labeling kit (Boerheinger Mannheim, Indianapolis, Ind.). Hybridization was conducted under high stringency conditions in a solution containing 50% formamide, 5×SSC, 50 mM NaPO4, pH 7.4, 1×Denhardts, 2% SDS and 100 ug/ml Salmon Sperm DNA at 42° C. overnight. The blots were washed with 2×SSC. at room temperature 2–3 times, followed, if necessary, by washes with 0.2×SSC, 0.1% SDS at 50° C. 1–2 times, and subjected to autoradiography at −80° C. The northern analysis demonstrated a high level of expression of an RNA species of ~1.3 kb from kidney, peripheral blood leukocytes, spleen and lymph nodes (FIG. 4). This RNA species was also expressed at a lower level in lung, bone marrow, thymus, and fetal liver. Since NHAP-2 has 89% homology to NHAP-1, the northern analysis reflected the expression profile of both NHAP-1 and NHAP-2. When the above blots were stripped and reprobed with NHAP-1-specific oligonucleotide, the expression of the 1.3 kb RNA species was found only in the lung (FIG. 5).

Analogous computer techniques applying BLAST were used to search for identical or related molecules in nucleotide databases such as GenBank or LIFESEQ database (Incyte Genomics).

The basis of the search is the product score, which is defined as:

$$\frac{\%\ \text{sequence identity} \times \%\ \text{maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis showed the transcript encoding NHAP in a variety of cDNA libraries, at least 59% of which involve cancer and immortalized cell lines, and at least 22% of which involve inflammation and the immune response. Abundance and percent abundance are also reported. Abundance directly reflects the number of times a particular transcript is represented in a cDNA library, and percent abundance is abundance divided by the total number of sequences examined in the cDNA library.

VI. Labeling and Use of Individual Hybridization Probes

Hybridization probes derived from SEQ ID NO:2 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 $\mu$Ci of [$\gamma$-$^{32}P$] adenosine triphosphate (Amersham Pharmacia Biotech), and T4 polynucleotide kinase (DuPont NEN, Boston, Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba1, or Pvu II (DuPont NEN).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. Hybridization patterns are visualized using autoradiography or an alternative imaging means and compared.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE (DNASTAR Inc). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the NHAP-encoding sequences, or any parts thereof, are used to detect, decrease, or inhibit expression of naturally occurring NHAP. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of NHAP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the NHAP-encoding transcript.

IX. Expression of NHAP-1

The cDNA encoding NHAP-1 was used to express full-length NHAP-1 by subcloning the cDNAs into appropriate vectors and introducing the constructs into host cells. For expression of NHAP-1 in *E.coli*, NHAP-1 cDNA was subcloned into a bacterial expression vector pET15b (Novagen, Inc., Madison, Wis.) which provides an N-terminal Tag of His6. To monitor expression in *E. coli*, the cell lysates from cultures before and after IPTG induction were separated using polyacrylamide gel electrophoresis under reduced denatured conditions, and probed with preimmune and immune serums (IC620). Binding of the antisera was detected by HRP-conjugated donkey anti-rabbit Ig and visualized using ECL (enhanced chemiluminescence) system (Amersham Pharmacia Biotech). NHAP-1 recombinant protein was detected as a ~45 kd band predominantly from the insoluble fraction in IPTG-induced cells exposed to immune serum (FIG. 6). A band was not detected in uninduced cells or cells probed with preimmune serum. NHAP-1 cDNA was also subcloned into the baculovirus pFast-bac-HTc (Life Technologies) for expression in Sf9 insect cells, and into pCMV-SPORT (Life Technologies) for expression in mammalian HEK 293 cells.

X. Demonstration of NHAP Activity

Protease activity of NHAP is measured by the hydrolysis of appropriate synthetic peptide substrates conjugated with various chromogenic molecules in which the degree of hydrolysis is quantitated by spectrophotometric (or fluorometric) absorption of the released chromophore. (Beynon, R. J. and J. S. Bond (1994) *Proteolytic Enzymes: A Practical Approach*, Oxford University Press, New York, N.Y., pp.25–55). Peptide substrates are designed according to the category of protease activity as endopeptidase (serine, cysteine, aspartic proteases), animopeptidase (leucine aminopeptidase), or carboxypeptidase (carboxypeptidase A and B, procollagen C-proteinase). Chromogens commonly used are 2-naphthylamine, 4-nitroaniline, and furylacrylic acid. Assays are performed at ambient temperature and contain an aliquot of the enzyme and the appropriate substrate in a suitable buffer. Reactions are carried out in an optical cuvette and followed by the increase/decrease in absorbance of the chromogen released during hydrolysis of the peptide substrate. The change in absorbance is proportional to the enzyme activity in the assay.

XI. Functional Assays

NHAP function is assessed by expressing the sequences encoding NHAP at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR™ 3.1 (Invitrogen, Carlsbad, Calif.), both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech,), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York, N.Y.

The influence of NHAP on gene expression can be assessed using highly purified populations of cells transfected with sequences encoding NHAP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding NHAP and other genes of interest can be analyzed by Northern analysis or microarray techniques.

XII. Production of NHAP Specific Antibodies

An oligopeptide containing 19 amino acid residues from the C-terminus of NHAP-1 was synthesized. Two rabbits were immunized with the oligopeptide-KLH complex in complete Freund's adjuvant (Zeneca LifeScience Molecules, Wilmington, Del.). The resulting antisera, IC619 and IC620, were tested for antipeptide activity by ELISA. Both antisera recognized recombinant protein expressed in *E.coli* and in Sf9 insect cells by western blot analysis. Briefly, *E.coli* and Sf9 cells containing the corresponding expression constructs were lysed, and proteins were separated on a denatured PAGE gel (NuPage gels, Novex) and transferred onto a nitrocellulose membrane according to the method previously described. The blot was then probed with antisera IC619 or IC620. Binding of the antisera was detected by HRP-conjugated donkey anti-rabbit Ig and visualized using ECL (enhanced chemiluminescence) system (Amersham Pharmacia Biotech).

XIII. Purification of Naturally Occurring NHAP Using Specific Antibodies

Naturally occurring or recombinant NHAP is substantially purified by immunoaffinity chromatography using antibodies specific for NHAP. An immunoaffinity column is constructed by covalently coupling anti-NHAP antibody to an activated chromatographic resin, such as CNBr-activated Sepharose (Amersham Pharmacia Biotech). After the coupling, the resin is blocked and washed according to the manufacturer's instructions.

Media containing NHAP are passed over the immunoaffinity column, and the column is washed under conditions that allow the preferential absorbance of NHAP (e.g., high ionic strength buffers in the presence of detergent). The column is eluted under conditions that disrupt antibody/NHAP binding (e.g., a buffer of pH 2 to pH 3, or a high concentration of a chaotrope, such as urea or thiocyanate ion), and NHAP is collected.

XIV Immunocytochemical Analysis of NHAP-1 in Normal and Disease Tissues

Immunocytochemical analysis was performed to determine protein localization in human tissue samples using NHAP-1-specific rabbit immune serum IC619 as the primary antibody. The analysis was performed by LifeSpan BioSciences, Inc., Seattle Wash. The detection system consisted of a DAKO LSAB+Kit (DAKO corp., Carpinteria Calif.) containing labelled Streptavidin-Biotin Kit with a biotinylated secondary antibody followed by application of a streptavidin-horseradish peroxidase conjugate and DAB substrate. Tissues were also blocked for endogenous biotin and endogenous peroxide. Negative controls performed on each tissue sample included staining with pre-immune sera. In addition, experiments were performed to block staining by incubating Antibody IC619 with a 10 fold excess of immunizing peptide derived from NAP1. The analysis demonstrated that antibody IC619 produced strong positive staining in the anterior lobe of the pituitary, in thyroid follicular cells and within the Type II pneumocytes of the lung. In all lung tissues examined, both normal and diseased, Type II pneumocytes stained positive for antibody IC619. In particular, the bronchioloalveolar carcinoma and lung adenocarcinoma produced strong positive staining. Other lung neoplasms including a small cell, epidermoid cell, adenocarcinoma and metastatic colon adenocarcinoma were negative when stained.

XV. Chromosome Localization of NHAP-1 and NHAP-2 by Fluorescence In Situ Hybridization (FISH) Analysis FISH analysis was performed to determine chromosomal localization of both NHAP-1 and NHAP-2 (Genome Systems, Inc., St. Louis, Mo.). DNA from two genomic clones, corresponding to NHAP-1 and NHAP-2, were labeled with digoxigenin dUTP by nick translation. Labeled probes were combined with sheared human DNA and independently hybridized to normal metaphase chromosomes derived from PHA stimulated peripheral blood lymphocytes from a male donor in a solution containing 50% formamide, 10% dextran sulfate and 2×SSC. Specific signals were detected by incubating the hybridized slides in fluoresceinated antidigoxigenin antibodies followed by counterstaining with DAPI. These experiments resulted in the specific labeling of the long arms of chromosome 19. Quantification of spreads with specific hybridization to chromosome 19 demonstrated that the genes encoding NHAP-1 and NHAP-2 are indistinguishable from each other and are located at a position which is 73% of the distance from the centromere to the telomere of chromosome arm 19q, an area that corresponds to band 19q13.3.

XVI. Identification of Molecules Which Interact with NHAP

NHAP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled NHAP, washed, and any wells with labeled NHAP complex are assayed. Data obtained using different concentrations of NHAP are used to calculate values for the number, affinity, and association of NHAP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Clone Number | Library Name | Library Description |
|---|---|---|
| 372637 | LUNGNOT02 | Library was constructed using RNA isolated from the lung tissue of a 47-year-old Caucasian male, who died of a subarachnoid hemorrhage. pBluescript |
| 2435410 | EOSINOT03 | Library was constructed using polyA RNA isolated from pooled eosinophils obtained from allergic asthmatic individuals. pSPORT1 |

TABLE 2

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch < 50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215:403–410; Altschul, S. F. et al. (1997) Nucleic Acids Res. 25:3389–3402. | ESTs: Probability value = 1.0E-8 or less<br>Full Length sequences: Probability value = 1.0E-10 or less |
| FASTA | A Pearson and Lipman algorithm that searches for similarity between a query sequence and a group of sequences of the same type. FASTA | Pearson, W. R. and D. J. Lipman (1988) Proc. Natl. Acad Sci. 85:2444–2448; Pearson, W. R. (1990) Methods Enzymol. 183:63–98; and | ESTs: fasta E value = 1.06E-6<br>Assembled ESTs: fasta Identity = 95% or greater and Match |

TABLE 2-continued

| Program | Description | Reference | Parameter Threshold |
|---|---|---|---|
| | comprises as least five functions: fasta, tfasta, fastx, tfastx, and ssearch. | Smith, T. F. and M. S. Waterman (1981) Adv. Appl. Math. 2:482–489. | length = 200 bases or greater; fastx E value = 1.0E-8 or less Full Length sequences: fastx score = 100 or greater |
| BLIMPS | A BLocks IMProved Searcher that matches a sequence against those in BLOCKS and PRINTS databases to search for gene families, sequence homology, and structural fingerprint regions. | Henikoff, S and J. G. Henikoff, Nucl. Acid Res., 19:6565–72, 1991. J. G. Henikoff and S. Henikoff (1996) Methods Enzymol. 266:88–105; and Attwood, T. K. et al. (1997) J. Chem. Inf. Comput. Sci. 37:417–424. | Score = 1000 or greater; Ratio of Score/Strength = 0.75 or larger; and Probability value = 1.0E-3 or less |
| PFAM | A Hidden Markov Models-based application useful for protein family search. | Krogh, A. et al. (1994) J. Mol. Biol., 235:1501–1531; Sonnhammer, E. L. L. et al. (1988) Nucleic Acids Res. 26:320–322. | Score = 10–50 bits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25:217–221. | Score = 4.0 or greater |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2:482–489; Smith, T. F. and M. S. Waterman (1981) J. Mol. Biol. 147:195–197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claverie, J. M. and S. Audie (1997) CABIOS 12:431–439. | Score = 5 or greater |
| Motifs | A program that searches amino acid sequences for patterns that matched those defined in Prosite. | Bairoch et al. <u>supra</u>; Wisconsin Package Program Manual, version 9, page M51–59, Genetics Computer Group, Madison, WI. | |

What is claimed is:

1. An isolated mammalian cDNA encoding a mammalian protein comprising an amino acid sequence of SEQ ID NO:3.

2. An isolated mammalian cDNA or the complement thereof comprising a nucleic acid sequence of SEQ ID NO:4.

3. A composition comprising the cDNA or the complement of the cDNA of claim 1.

4. A substrate comprising the cDNA or the complement of the cDNA of claim 1.

5. A probe comprising the cDNA or the complement of the cDNA of claim 1.

6. A vector comprising the cDNA of claim 1.

7. A host cell comprising the vector of claim 6.

8. A method for producing a protein, the method comprising:

a) culturing the host cell of claim 7 under conditions for protein expression; and b) recovering the protein from the host cell culture.

9. A method for detecting a polynucleotide in a sample, the method comprising the steps of:

(a) hybridizing the probe of claim 5 to at least one of the nucleic acids in the sample, thereby forming a hybridization complex; and (b) detecting the hybridization complex, wherein the presence of the hybridization complex correlates with the presence of the polynucleotide in the sample.

10. The method of claim 9 further comprising amplifying the nucleic acids of the sample prior to hybridization.

11. A method of using a cDNA to screen a plurality of molecules or compounds, the method comprising:

a) combining the cDNA of claim 1 with a plurality of molecules or compounds under conditions to allow specific binding; and b) detecting specific binding, thereby identifying a molecule or compound which specifically binds the cDNA.

12. The method of claim 11 wherein the molecules or compounds are selected from DNA molecules, RNA molecules, peptide nucleic acids, artificial chromosome constructions, peptides, transcription factors, and regulatory molecules.

13. A method of using a polynucleotide to purify a molecule or compound from a sample, the method comprising:

a) combining a polynucleotide of claim 1 with a sample under conditions to allow specific binding;

b) recovering the bound polynucleotide; and c) separating the polynucleotide from the molecule or compound, thereby obtaining purifed molecule or compound.

* * * * *

SEQUENCE LISTING

```
<160> NUMBER OF SEQ ID NOS: 10

<210> SEQ ID NO 1
<211> LENGTH: 420
<212> TYPE: PRT
<213> ORGANISM: HOMO SAPIENS
<220> FEATURE:
<223> OTHER INFORMATION: 372637, LUNGNOT02

<400> SEQUENCE: 1

Met Ser Pro Pro Pro Leu Leu Gln Pro Leu Leu Leu Leu Leu Pro Leu
 1               5                  10                  15

Leu Asn Val Glu Pro Ser Gly Ala Thr Leu Ile Arg Ile Pro Leu His
            20                  25                  30

Arg Val Gln Pro Gly Arg Arg Thr Leu Asn Leu Leu Arg Gly Trp Arg
        35                  40                  45

Glu Pro Ala Glu Leu Pro Lys Leu Gly Ala Pro Ser Pro Gly Asp Lys
    50                  55                  60

Pro Ile Phe Val Pro Leu Ser Asn Tyr Arg Asp Val Gln Tyr Phe Gly
65                  70                  75                  80

Glu Ile Gly Leu Gly Thr Pro Pro Gln Asn Phe Thr Val Ala Phe Asp
                85                  90                  95

Thr Gly Ser Ser Asn Leu Trp Val Pro Ser Arg Arg Cys His Phe Phe
            100                 105                 110

Ser Val Pro Cys Trp Leu His His Arg Phe Asp Pro Lys Ala Ser Ser
        115                 120                 125
```

-continued

```
Ser Phe Gln Ala Asn Gly Thr Lys Phe Ala Ile Gln Tyr Gly Thr Gly
    130                 135                 140

Arg Val Asp Gly Ile Leu Ser Glu Asp Lys Leu Thr Ile Gly Gly Ile
145                 150                 155                 160

Lys Gly Ala Ser Val Ile Phe Gly Glu Ala Leu Trp Glu Pro Ser Leu
                165                 170                 175

Val Phe Ala Phe Ala His Phe Asp Gly Ile Leu Gly Leu Gly Phe Pro
            180                 185                 190

Ile Leu Ser Val Glu Gly Val Arg Pro Pro Met Asp Val Leu Val Glu
        195                 200                 205

Gln Gly Leu Leu Asp Lys Pro Val Phe Ser Phe Tyr Leu Asn Arg Asp
    210                 215                 220

Pro Glu Glu Pro Asp Gly Gly Glu Leu Val Leu Gly Gly Ser Asp Pro
225                 230                 235                 240

Ala His Tyr Ile Pro Pro Leu Thr Phe Val Pro Val Thr Val Pro Ala
                245                 250                 255

Tyr Trp Gln Ile His Met Glu Arg Val Lys Val Gly Pro Gly Leu Thr
            260                 265                 270

eu Cys Ala Lys Gly Cys Ala Ala Ile Leu Asp Thr Gly Thr Ser Leu
        275                 280                 285

Ile Thr Gly Pro Thr Glu Glu Ile Arg Ala Leu His Ala Ala Ile Gly
    290                 295                 300

Gly Ile Pro Leu Leu Ala Gly Glu Tyr Ile Ile Leu Cys Ser Glu Ile
305                 310                 315                 320

Pro Lys Leu Pro Ala Val Ser Phe Leu Leu Gly Gly Val Trp Phe Asn
                325                 330                 335

Leu Thr Ala His Asp Tyr Val Ile Gln Thr Thr Arg Asn Gly Val Arg
            340                 345                 350

Leu Cys Leu Ser Gly Phe Gln Ala Leu Asp Val Pro Pro Pro Ala Gly
        355                 360                 365

Pro Phe Trp Ile Leu Gly Asp Val Phe Leu Gly Thr Tyr Val Ala Val
    370                 375                 380

Phe Asp Arg Gly Asp Met Lys Ser Ser Ala Arg Val Gly Leu Ala Arg
385                 390                 395                 400

Ala Arg Thr Arg Gly Ala Asp Leu Gly Trp Gly Glu Thr Ala Gln Ala
                405                 410                 415

Gln Phe Pro Gly
            420


<210> SEQ ID NO 2
<211> LENGTH: 2061
<212> TYPE: DNA
<213> ORGANISM: HOMO SAPIENS
<220> FEATURE:
<223> OTHER INFORMATION: 877617, LUNGAST01

<400> SEQUENCE: 2

cttgagagct ctcaaatact tggtcatgga tgaagccgac cgaatactga atatggattt     60

tgagacagag gttgacaagc ctcgagatcg gaaaacattc ctcttctctg ccaccatgac    120

caagaaggtt caaaaacttc agcgagcagc tctgaagaat cctgtgaaat gtgccgtttc    180

ctctaaatac cagacagttg aaaaattaca gcaatattat atttttattc cctctaaatt    240

caaggatacc tacctggttt atattctaaa tgaattggct ggaaactcct ttatgatatt    300

ctgcagcacc tgtaataata cccagagaac agctttgcta ctgcgaaatc ttggcttcac    360
```

-continued

```
tgccatcccc ctccatggac aaatgagtca gagtaagcgc ctaggatccc ttaataagtt    420

taaggccaag gcccgttcca ttcttctagc aactgacgtt gccagccgag gtttggacat    480

acctcatgta gatgtggttg tcaactttga cattcctacc cattccaagg attacatcca    540

tcgagtaggt cgaacagcta gagctgggcg ctccggaaag gctattactt ttgtcacaca    600

gtatgatgtg gaactcttcc agcgcataga acacttaatt gggaagaaac taccaggttt    660

tccaacacag gatgatgagg ttatgatgct gacagaacgc gtccccagcg atgtctccac    720

caccgctgct gcaacccctg ctgctgctgc tgcctctgct gaatgtggag ccttccgggg    780

ccacactgat ccgcatccct cttcatcgag tccaacctgg acgcaggacc ctgaacctac    840

tgaggggatg gagagaacca gcagagctcc ccaagttggg ggccccatcc cctggggaca    900

agcccatctt cgtacctctc tcgaactaca gggatgtgca gtattttggg gaaattgggc    960

tgggaacgcc tccacaaaac ttcactgttg cctttgacac tggctcctcc aatctctggg   1020

tcccgtccag gagatgccac ttcttcagtg tgccctgctg gttacaccac cgatttgatc   1080

ccaaagcctc tagctccttc caggccaatg ggaccaagtt tgccattcaa tatggaactg   1140

ggcgggtaga tggaatcctg agcgaggaca agctgactat tggtggaatc aagggtgcat   1200

cagtgatttt cggggaggct ctctgggagc ccagcctggt cttcgctttt gcccattttg   1260

atgggatatt gggcctcggt tttcccattc tgtctgtgga aggagttcgg cccccgatgg   1320

atgtactggt ggagcagggg ctattggata agcctgtctt ctccttttac ctcaacaggg   1380

accctgaaga gcctgatgga ggagagctgg tcctgggggg ctcggacccg gcacactaca   1440

tcccacccct caccttcgtg ccagtcacgg tccctgccta ctggcagatc cacatggagc   1500

gtgtgaaggt gggcccaggg ctgactctct gtgccaaggg ctgtgctgcc atcctggata   1560

cgggcacgtc cctcatcaca ggacccactg aggagatccg ggccctgcat gcagccattg   1620

ggggaatccc cttgctggct ggggagtaca tcatcctgtg ctcggaaatc ccaaagctcc   1680

ccgcagtctc cttccttctt ggggggtct ggtttaacct cacggcccat gattacgtca   1740

tccagactac tcgaaatggc gtccgcctct gcttgtccgg tttccaggcc ctggatgtcc   1800

ctccgcctgc agggcccttc tggatcctcg gtgacgtctt cttggggacg tatgtggccg   1860

tcttcgaccg cggggacatg aagagcagcg cccgggtggg cctggcgcgc gctcgcactc   1920

gcggagcgga cctcggatgg ggagagactg cgcaggcgca gttccccggg tgacgcccaa   1980

gtgaagcgca tgcgcagcgg gtggtcgcgg aggtcctgct acccagtaaa aatccactat   2040

tgccattgaa aaaaaaaaaa a                                             2061
```

<210> SEQ ID NO 3
<211> LENGTH: 433
<212> TYPE: PRT
<213> ORGANISM: HOMO SAPIENS
<220> FEATURE:
<221> NAME/KEY: unsure
<222> LOCATION: 322
<223> OTHER INFORMATION: 2435410, EOSINOT03

<400> SEQUENCE: 3

```
Met Ser Pro Pro Leu Leu Leu Leu Pro Leu Leu Leu Leu Leu Pro Leu
 1               5                  10                  15

Leu Asn Val Glu Pro Ala Gly Ala Thr Leu Ile Arg Ile Pro Leu Arg
            20                  25                  30

Gln Val His Pro Gly Arg Arg Thr Leu Asn Leu Leu Arg Gly Trp Gly
        35                  40                  45
```

-continued

```
Lys Pro Ala Glu Leu Pro Lys Leu Gly Ala Pro Ser Pro Gly Asp Lys
    50                  55                  60

Pro Ala Ser Val Pro Leu Ser Lys Phe Leu Asp Ala Gln Tyr Phe Gly
65                  70                  75                  80

Glu Ile Gly Leu Gly Thr Pro Pro Gln Asn Phe Thr Val Ala Phe Asp
                85                  90                  95

Thr Gly Ser Ser Asn Leu Trp Val Pro Ser Arg Arg Cys His Phe Phe
            100                 105                 110

Ser Val Pro Cys Trp Phe His His Arg Phe Asn Pro Asn Ala Ser Ser
        115                 120                 125

Ser Phe Lys Pro Ser Gly Thr Lys Phe Ala Ile Gln Tyr Gly Thr Gly
    130                 135                 140

Arg Val Asp Gly Ile Leu Ser Glu Asp Lys Leu Thr Ile Gly Gly Ile
145                 150                 155                 160

Lys Gly Ala Ser Val Ile Phe Gly Glu Ala Leu Trp Glu Ser Ser Leu
                165                 170                 175

Val Phe Thr Val Ser Arg Pro Asp Gly Ile Leu Gly Leu Gly Phe Pro
            180                 185                 190

Ile Leu Ser Val Glu Gly Val Arg Pro Pro Leu Asp Val Leu Val Glu
        195                 200                 205

Gln Gly Leu Leu Asp Lys Pro Val Phe Ser Phe Tyr Phe Asn Arg Asp
    210                 215                 220

Pro Glu Val Ala Asp Gly Gly Glu Leu Val Leu Gly Gly Ser Asp Pro
225                 230                 235                 240

Ala His Tyr Ile Pro Pro Leu Thr Phe Val Pro Val Thr Val Pro Ala
                245                 250                 255

Tyr Trp Gln Ile His Met Glu Arg Val Lys Val Gly Ser Arg Leu Thr
            260                 265                 270

Leu Cys Ala Gln Gly Cys Ala Ala Ile Leu Asp Thr Gly Thr Pro Val
        275                 280                 285

Ile Val Gly Pro Thr Glu Glu Ile Arg Ala Leu His Ala Ala Ile Gly
    290                 295                 300

Gly Ile Pro Leu Leu Ala Gly Glu Tyr Ile Ile Arg Cys Ser Lys Ile
305                 310                 315                 320

Pro Xaa Leu Pro Ala Val Ser Leu Leu Ile Gly Gly Val Trp Phe Asn
                325                 330                 335

Leu Thr Ala Gln Asp Tyr Val Ile Gln Phe Ala Gln Gly Asp Val Arg
            340                 345                 350

Leu Cys Leu Ser Gly Phe Arg Ala Leu Asp Ile Ala Ser Pro Pro Val
        355                 360                 365

Pro Val Trp Ile Leu Gly Asp Val Phe Leu Gly Ala Tyr Val Thr Val
    370                 375                 380

Phe Asp Arg Gly Asp Met Lys Ser Gly Ala Arg Val Gly Leu Ala Arg
385                 390                 395                 400

Ala Arg Pro Arg Gly Ala Asp Leu Gly Arg Arg Glu Thr Ala Gln Ala
                405                 410                 415

Gln Tyr Arg Gly Cys Arg Pro Gly Asp Ala His Ala His Arg Val Ala
            420                 425                 430

Ser

<210> SEQ ID NO 4
<211> LENGTH: 1329
<212> TYPE: DNA
```

-continued

<213> ORGANISM: HOMO SAPIENS
<220> FEATURE:
<223> OTHER INFORMATION: 2435410, EOSINOT03

<400> SEQUENCE: 4
gaattccggg tcgaccacgc gtccgcagca atgtctccac cactgctgct gctacccttg 60
ctgctgctgc tgcctctgct gaatgtggag cctgctgggg ccacactgat ccggatccct 120
cttcgtcaag tccaccctgg acgcaggacc ctgaacctac tgaggggatg ggaaaaacca 180
gcagagctcc ccaagttggg ggccccatcc cctggggaca agcctgcctc ggtacctctc 240
tccaaattcc tggatgccca gtattttggg gaaattgggc tgggaacgcc tccacaaaac 300
ttcactgttg cctttgacac tggctcctcc aatctctggg tcccgtccag gagatgccac 360
ttcttcagtg tgccctgctg gttccaccac cgcttcaatc ccaatgcctc cagctccttc 420
aagcccagtg ggaccaagtt tgccattcag tatggaactg ggcgggtaga tggaatcctg 480
agtgaggaca agctgactat tggtggaatc aagggtgcat ccgtgatttt cggggaagct 540
ctgtgggaat ccagcctggt cttcactgtt tcccgccccg atgggatatt gggcctcggt 600
tttcccattc tgtctgtgga aggagttcgg cccccgctgg atgtactggt ggagcagggg 660
ctattggata agcctgtctt ctccttttac ttcaacaggg accctgaagt ggctgatgga 720
ggagagctgg tcctgggggg ctcagacccg gcacactaca tcccacccct caccttcgtg 780
ccagtcacag tccccgccta ctggcagatc cacatggagc gtgtgaaggt gggctcacgg 840
ctgactctct gtgcccaggg ctgtgctgcc atcctggata caggcacacc tgtcatcgta 900
ggacccactg aggagatccg ggccctgcat gcagccattg gggaatcccc cttgctggct 960
ggggagtaca tcatccggtg ctcagaaatc ccaaagctcc ccgcagtctc actcctcatt 1020
gggggggtct ggtttaatct cacggcccag gattacgtca tccagtttgc tcagggtgac 1080
gtccgcctct gcttgtccgg cttccgggcc ttggacatcg cttcgcctcc agtacctgtg 1140
tggatcctcg gcgacgtttt cttgggggcg tatgtgaccg tcttcgaccg cggggacatg 1200
aagagcggcg cacgagtggg actggcgcgc gctcgccctc gcggagcgga cctgggaagg 1260
cgcgagaccg cgcaggcgca gtaccgcggg tgccgcccag gtgatgcgca tgcgcaccgg 1320
gtagcagag 1329

<210> SEQ ID NO 5
<211> LENGTH: 186
<212> TYPE: DNA
<213> ORGANISM: HOMO SAPIENS
<220> FEATURE:
<223> OTHER INFORMATION: 372637H1, LUNGNOT02
<221> NAME/KEY: unsure
<222> LOCATION: (0)...(0)
<223> OTHER INFORMATION: 182, 182

<400> SEQUENCE: 5
ggagatgcca cttcttcagt gtgccctgct ggttacacca ccgatttgat cccaaagcct 60
ctagctcctt ccaggccaat gggaccaagt ttgccattca atatggaact gggcgggtag 120
atggaatcct gagcgaggac aagctgacta ttggtggaat caagggtgca tcagtgattt 180 tngggt 186

<210> SEQ ID NO 6
<211> LENGTH: 227
<212> TYPE: DNA
<213> ORGANISM: HOMO SAPIENS
<220> FEATURE:

```
<223> OTHER INFORMATION: 124290H1, LUNGNOT03

<400> SEQUENCE: 6

tgggctggga acgcctccac aaaacttcac tgttgccttt gacactggct cctccaatct      60

ctgggtcccg tccaggagat gccacttctt cagtgtgccc tgctggttac accaccgatt     120

tgatcccaaa gcctctagct ccttccaggc caatgggacc aagtttgcca ttcaatatgg     180

aactgggcgg gtagatggaa tctgagcgag gacaagctga ctattgg                   227

<210> SEQ ID NO 7
<211> LENGTH: 160
<212> TYPE: DNA
<213> ORGANISM: HOMO SAPIENS
<220> FEATURE:
<223> OTHER INFORMATION: 2222291H1, LUNGNOT18
<221> NAME/KEY: unsure
<222> LOCATION: (2)...(2)
<221> NAME/KEY: unsure
<222> LOCATION: (8)...(8)
<221> NAME/KEY: unsure
<222> LOCATION: (18)...(18)
<221> NAME/KEY: unsure
<222> LOCATION: (49)...(49)
<221> NAME/KEY: unsure
<222> LOCATION: (59)...(59)
<221> NAME/KEY: unsure
<222> LOCATION: (128)...(128)
<221> NAME/KEY: unsure
<222> LOCATION: (132)...(132)

<400> SEQUENCE: 7

cncccggntg ggcctggngc gcgctcgcac tcgcggagcg gaacctcgna tggggagana      60

ctgcgcaggc gcagttcccc gggtgacgcc caagtgaagc gcatgcgcac gggtggtcgc     120

ggaggtcntg cnacccagta aaaatccact atttccattg                            160

<210> SEQ ID NO 8
<211> LENGTH: 215
<212> TYPE: DNA
<213> ORGANISM: HOMO SAPIENS
<220> FEATURE:
<223> OTHER INFORMATION: 2435410H1, EOSINOT03
<221> NAME/KEY: unsure
<222> LOCATION: (85)...(85)

<400> SEQUENCE: 8

cagacccggc acactacatc ccacccctca ccttcgtgcc agtcacagtc cgcgcctact      60

ggcagatcca caatgagcgt gtganggtgg gctcacggct gactctctgt tcccagggct     120

gtgctgccat cctggataca ggcacacctg tcatcgtagg acccactgag gagatccggg     180

ccctgcatgc agccattggg ggaatcccct tgctg                                 215

<210> SEQ ID NO 9
<211> LENGTH: 289
<212> TYPE: DNA
<213> ORGANISM: HOMO SAPIENS
<220> FEATURE:
<223> OTHER INFORMATION: 2756549H1, THP1A2S08
<221> NAME/KEY: unsure
<222> LOCATION: (267)...(267)
<221> NAME/KEY: unsure
<222> LOCATION: (277)...(277)

<400> SEQUENCE: 9

cttcactgtt gcctttgaca ctggctcctc caatctctgg gtcccgtcca ggagatgcca      60

cttcttcagt gtgccctgct ggttccacca ccgcttcaat cccaatgcct ccagctcctt     120
```

-continued

```
caagcccagt gggaccaagt ttgccattca gtatggaact gggcgggtag atggaatcct    180

gagtgaggac aagctgacta ttggtggaat caagggtgca tccgtgattt tcggggaagc    240

tctgtgggaa tccagcctgg tcttcantgt ttcncgnccc gatgggata                289


<210> SEQ ID NO 10
<211> LENGTH: 419
<212> TYPE: PRT
<213> ORGANISM: MUS MUSCULUS
<220> FEATURE:
<223> OTHER INFORMATION: 1906810, GenBank

<400> SEQUENCE: 10

Met Ser Pro Leu Leu Leu Leu Leu Leu Cys Leu Leu Leu Gly Asn Leu
 1               5                  10                  15

Glu Pro Glu Glu Ala Lys Leu Ile Arg Val Pro Leu Gln Arg Ile His
            20                  25                  30

Leu Gly His Arg Ile Leu Asn Pro Leu Asn Gly Trp Glu Gln Leu Ala
        35                  40                  45

Glu Leu Ser Arg Thr Ser Thr Ser Gly Gly Asn Pro Ser Phe Val Pro
    50                  55                  60

Leu Ser Lys Phe Met Asn Thr Gln Tyr Phe Gly Thr Ile Gly Leu Gly
65                  70                  75                  80

Thr Pro Pro Gln Asn Phe Thr Val Val Phe Asp Thr Gly Ser Ser Asn
                85                  90                  95

Leu Trp Val Pro Ser Thr Arg Cys His Phe Phe Ser Leu Ala Cys Trp
            100                 105                 110

Phe His His Arg Phe Asn Pro Lys Ala Ser Ser Ser Phe Arg Pro Asn
        115                 120                 125

Gly Thr Lys Phe Ala Ile Gln Tyr Gly Thr Gly Arg Leu Ser Gly Ile
    130                 135                 140

Leu Ser Gln Asp Asn Leu Thr Ile Gly Gly Ile His Asp Ala Phe Val
145                 150                 155                 160

Thr Phe Gly Glu Ala Leu Trp Glu Pro Ser Leu Ile Phe Ala Leu Ala
                165                 170                 175

His Phe Asp Gly Ile Leu Gly Leu Gly Phe Pro Thr Leu Ala Val Gly
            180                 185                 190

Gly Val Gln Pro Pro Leu Asp Ala Met Val Glu Gln Gly Leu Leu Glu
        195                 200                 205

Lys Pro Val Phe Ser Phe Tyr Leu Asn Arg Asp Ser Glu Gly Ser Asp
    210                 215                 220

Gly Gly Glu Leu Val Leu Gly Gly Ser Asp Pro Ala His Tyr Val Pro
225                 230                 235                 240

Pro Leu Thr Phe Ile Pro Val Thr Ile Pro Ala Tyr Trp Gln Val His
                245                 250                 255

Met Glu Ser Val Lys Val Gly Thr Gly Leu Ser Leu Cys Ala Gln Gly
            260                 265                 270

Cys Ser Ala Ile Leu Asp Thr Gly Thr Ser Leu Ile Thr Gly Pro Ser
        275                 280                 285

Glu Glu Ile Arg Ala Leu Asn Lys Ala Ile Gly Gly Tyr Pro Phe Leu
    290                 295                 300

Asn Gly Gln Tyr Phe Ile Gln Cys Ser Lys Thr Pro Thr Leu Pro Pro
305                 310                 315                 320

Val Ser Phe His Leu Gly Gly Val Trp Phe Asn Leu Thr Gly Gln Asp
                325                 330                 335
```

-continued

```
Tyr Val Ile Lys Ile Leu Gln Ser Asp Val Gly Leu Cys Leu Leu Gly
            340                 345                 350

Phe Gln Ala Leu Asp Ile Pro Lys Pro Ala Gly Pro Leu Trp Ile Leu
        355                 360                 365

Gly Asp Val Phe Leu Gly Pro Tyr Val Ala Val Phe Asp Arg Gly Asp
    370                 375                 380

Lys Asn Val Gly Pro Arg Val Gly Leu Ala Arg Ala Gln Ser Arg Ser
385                 390                 395                 400

Thr Asp Arg Ala Glu Arg Arg Thr Thr Gln Ala Gln Phe Phe Lys Arg
                405                 410                 415

Arg Pro Gly
```